United States Patent [19]
Wilson et al.

[11] Patent Number: 6,018,058
[45] Date of Patent: Jan. 25, 2000

[54] 1,4 DIHYDRODIOXINS AND RELATED COMPOUNDS AS DNA CLEAVING REAGENTS

[75] Inventors: Robert M. Wilson; Karlyn A. Schnapp; Andreas Harsch; Stephen J. Keller; Donna J. Schlemm, all of Cincinnati, Ohio

[73] Assignee: University of Cincinnati, Cincinnati, Ohio

[21] Appl. No.: 08/860,481

[22] PCT Filed: Dec. 21, 1995

[86] PCT No.: PCT/US95/16434

§ 371 Date: Sep. 30, 1997

§ 102(e) Date: Sep. 30, 1997

[87] PCT Pub. No.: WO96/20205

PCT Pub. Date: Jul. 4, 1996

[51] Int. Cl.⁷ ........................ C07D 319/22; C07H 21/00
[52] U.S. Cl. .................. 549/358; 435/6; 514/44; 514/410; 514/453; 536/23.1; 536/24.5; 536/25.3
[58] Field of Search .................. 544/358; 514/44, 514/453, 410; 536/23.1, 24.5, 25.3; 435/6

[56] References Cited

U.S. PATENT DOCUMENTS

| | | | |
|---|---|---|---|
| 4,699,978 | 10/1987 | Barton | 536/27 |
| 5,162,218 | 11/1992 | Schultz | 435/188 |
| 5,258,506 | 11/1993 | Urdea et al. | 536/23.1 |

OTHER PUBLICATIONS

Fang, C.A. 106:196342, 1987.

Bregant, T.M.; Groppe, J.; Little, R.D.; J. Am. Chem. Soc. (1994) 116: 3635–3636.

Dervan and Becker, J. Am. Chem. Soc. (1978) 100: 1968–1970.

Morri, et al, J. Am. Chem. Soc. (1993) 115: 1150–1151.

Armitage, et al, J. Am. Chem. Soc. (1994) 116: 9847–9859.

Sitlani, et al, J. Am. Chem. Soc. (1992) 114: 2303–2312.

Pfundt, et al., Tetrahedron (1966) 22:2237–2247.

*Primary Examiner*—Robert Gerstl
*Attorney, Agent, or Firm*—Frost & Jacobs LLP

[57] ABSTRACT

The present invention relates to a class of 1,4-dihydrodioxin masked quinone compounds which are useful as DNA or RNA cleaving reagents. These compounds may additionally include moieties which target the compounds to specific base sequences on the DNA or RNA molecule to permit site-specific cleavage. The process for using these compounds in a UV or short wavelength visible light-activated reaction for cleaving DNA, as well as pharmaceutical compositions containing these compounds, are also disclosed.

38 Claims, No Drawings

1,4 DIHYDRODIOXINS AND RELATED COMPOUNDS AS DNA CLEAVING REAGENTS

This application is a continuation-in-part of U.S. patent application Ser. No. 08/365,091, Wilson, et al., filed Dec. 28, 1994. +gi

STATEMENT REGARDING FEDERAL FUNDING OF RESEARCH

This research was carried out, in part, under National Science Foundation Grant CHE-8914889.

TECHNICAL FIELD

This invention relates to biochemical reagents used in the manipulation of genetic material, and, particularly, to compounds which can cleave DNA or RNA molecules at specifically defined locations.

BACKGROUND OF THE INVENTION

It is well known that deoxyribonucleic acid (DNA) is a helically-shaped double stranded molecule having complementary base pairs connecting the two phosphate-sugar backbone strands. The ability to cleave DNA or RNA, both single strand and double strand, is important. It is particularly important that it be possible to direct this cleavage such that it occurs at specifically-defined sites in the DNA or RNA molecule. Such DNA and RNA cleavage agents could be useful in a laboratory setting for biological or pharmaceutical research or as part of a diagnostic tool. It is also possible that such agents could be used in vivo as part of a gene therapy regimen, for example in the treatment of cancer.

At the present time, there are several types of reagents that can be used to cleave DNA either thermally or photochemically. These include (1) dienyne natural products and their synthetic derivatives; (2) other reagents that generate biradicals, e.g., azoalkenes; (3) organoplatinum reagents; (4) anthraquinones; and (5) rhodium and ruthenium complexes. The dienyne products and their derivatives are very complex molecules that will cleave DNA either thermally or photochemically. This DNA cleaving activity is thought to be the source of their activity against certain types of cancer. These compounds, however, are not readily available. The need to isolate these materials from their natural sources makes it difficult to obtain dienynes in large quantities at reasonable prices. Even if these compounds were synthesized chemically, the synthesis would involve multiple step reactions just to prepare the active molecules, not to mention the additional synthetic effort that would be necessary to attach them to DNA sequence specific groups. Thus, the dienyne materials do not offer a cost-effective way of cleaving DNA molecules.

Azoalkenes that form trimethylenemethane biradicals (see Bregant, T. M.; Groppe, J.; Little, R. D.; *J. Am. Chem. Soc.* 1994, 116: 3635–3636) are thermally unstable and decompose over several days at room temperature.

Anthraquinones are para-quinones that are highly reactive and sensitive to visible light. They will destroy their own sequence-recognition chains unless stored in the cold and rigorously protected from visible light.

Organoplatinum reagents have also been shown to be effective for the photochemical cleavage of DNA. Here again, these reagents are relatively expensive to produce in bulk quantities and are not particularly amenable to the synthetic modification which is necessary if DNA sequence recognition properties are to be incorporated into them. Furthermore, the toxicological properties of these materials can become a problem when used in vivo, for example in the treatment of cancer.

Rhodium and ruthenium complexes have also been shown to be effective as photochemical agents for the cleavage of DNA. However, like the organoplantinum complexes, they are expensive to manufacture and could pose significant toxicological risks if they are to be used in vivo.

There is, therefore, a need for DNA cleavage reagents which are easy to synthesize in bulk quantities, which are relatively stable on storage and will survive to reach their target site in the cell, which do not involve the cost, availability or toxicological issues present with the precious metal compounds, and which may easily be modified to bind to specific DNA sequences and, therefore, cleave DNA at specifically defined sites. It is this problem which the present invention seeks to address.

Dervan and Becker, *J. Am. Chem. Soc.* (1978) 100: 1968–1970, describes the synthesis and use of bis (methidium) spermine as a polyintercalating molecule (i.e., a molecule which simultaneously binds to adjacent sites of DNA). The approach taken in this work was to form a dimer of ethidium bromide, a known intercalating molecule, using spermine as the linking group. The molecules described in this paper are not taught to be useful to cleave DNA.

Morii, et al, *J. Am. Chem. Soc.* (1993) 115: 1150–1151, studied the sequence- specific DNA binding of certain peptide dimers and found that certain enantiomers bind better than others. The molecule used to link the sequence-recognizing monomers was 9,10-dihydrophenanthrene-9, 10-diol, a planar moiety. The molecules described in this paper are not taught to be useful to cleave DNA.

Armitage, et al, *J. Am. Chem. Soc.* (1994) 116: 9847–9859, studied the use of certain para-quinone compounds, i.e., amide and ammonium-substituted anthraquinones, as photocatalytic DNA cleaving agents.

Sitlani, et al, *J. Am. Chem. Soc.* (1992) 114: 2303–2312, studied phenanthrenequinone diimine complexes of rhodium (III) and concluded that they promote DNA cleavage in the presence of ultraviolet light.

U.S. Pat. No. 4,699,978, Barton, issued Oct. 13, 1987, describes bis-substituted ruthenium or cobalt metal complexes of phenanthrolines which bind stereospecifically to DNA and can be used to cleave DNA in the presence of ultraviolet light.

U.S. Pat. No. 5,258,506, Urdea, et al, issued Nov. 2, 1993, deals with a particular family of chemicals which are suitable for being incorporated into oligonucleotide chains so as to introduce sites which may be cleaved by exposure to ultraviolet light. The materials disclosed in this patent are not, themselves, used to cut naturally occurring DNA strands at desired sites. Rather, they would be incorporated into the DNA molecules of interest via hybridization, and the resulting complex would be cleaved at the site at which the materials are situated.

U.S. Pat. No. 5,162,218, Schultz, issued Nov. 10, 1992, describes a means for attaching a polypeptide to a binding site to provide an active functionality at that site. The functionality allows reporter molecules having therapeutic or catalytic activity to bind at the site.

Pfundt, et al., *Tetrahedron* 22(7):2237–2247 (1966) [abstract at Chem. Abs. 65: 10474a (1966)], describes the determination, by NMR spectroscopy, of the conformation of various 1,4-dioxene derivatives. There is no suggestion that these compounds could be used in cleaving DNA.

The Arnitage, et al and Sitlani, et al papers and the Barton patent all disclose compounds useful in the photocatalytic cleavage of DNA. These molecules all incorporate planar moieties in order to achieve intercalation. However, none of these disclosures utilize the "masked quinone" approach of the present invention which allows the molecule to embed itself in and cleave DNA, but not react with other cell components. The Pfundt, et al., article which describes compounds similar to those used in the present invention, does not suggest their use in a biological context.

SUMMARY OF THE INVENTION

The present invention relates to DNA cleaving reagents having the formula:

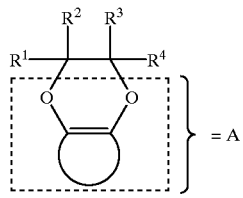

wherein A is a moiety capable either of intercalation between DNA base pairs or groove binding (such as 1,4-dihydrodioxins derived from phenanthrenequinones, acenaphthenequinones and other aromatic molecules, steroid-derived molecules, polypyrroles, CC-1065 analogs, and imidazole or thiazole analogs of CC-1065), and $R^1$, $R^2$, $R^3$ and $R^4$ are each selected from the group consisting of phenyl, substituted phenyl, aryl, alkyl, substituted alkyl, $C_4$-$C_8$ heterocyclic rings, and polypyrroles, with at least one of said R groups being aromatic. These reagents also are useful for cleaving RNA.

In addition, the present invention relates to the complex formed by these DNA cleaving reagents with DNA, as well as pharmaceutical compositions containing the defined DNA cleaving reagents together with pharmaceutical carriers.

Finally, the present invention relates to a process for cleaving DNA comprising the steps of combining an aqueous solution of the DNA cleaving reagent, defined above, having a concentration of no more than about 1M, preferably from about 1 to about 200 $\mu$M, most preferably from about 50 to about 200 $\mu$M, with a solution of DNA, having a concentration of from about 1 to about 100 $\mu$M in base pairs, at a temperature of from about 20 to about 37° C. and a pH of from about 6.9 to about 8.5, and irradiating said combined solutions with light having a wavelength of from about 333 to about 550 nm (preferably from about 333 to about 500 nm) for a period of from about 10 seconds to about 30 minutes (preferably from about 10 seconds to about 5 minutes).

All percentages and ratios used herein are "by weight" unless otherwise specified.

DETAILED DESCRIPTION OF THE INVENTION

Broadly defined, the DNA cleaving reagents of the present invention are ortho-quinones or 1,2-dicarbonyl compounds that have been masked as dihydrodioxin units by means of a template unit. When the compounds contain DNA base pair sequence-recognizing units, the template unit also serves to orient the dihydrodioxin intercalating or groove binding terminus with respect to the DNA sequence-recognizing terminus in a geometry that optimizes the binding of the entire molecule in either the major or minor groove of a DNA molecule. Each of the DNA cleaving reagents of the present invention is constructed from at least the first two of the following constituents:

A. The masked cleaving unit (MCU—also referred to as A in this application). Irradiation of this unit with ultraviolet or short wavelength visible light will produce its efficient fragmentation to an ortho-quinone or 1,2-dicarbonyl compound. This released quinone is believed to be the species which actually produces the DNA cleavage. In its masked form, the cleaving agent exists as a dihydrodioxin which is relatively inert and assocates itself with the DNA base pairs much more efficiently than does the quinone itself. Upon photochemical release, the quinone is associated (complexed) at a specific location in the DNA lattice and is appropriately oriented for cleaving the DNA sugar-phosphate backbone at that location.

B. The template unit (TU). This unit acts to mask the DNA cleaving agent and usually serves to link it to the DNA sequence-recognizing units, when those units are used in the present invention. In most instances, the template unit will be chiral, having the appropriate chirality to coordinate the intercalation or groove binding of the masked cleaving agent and the orientation of the sequence-recognizing units with DNA groove chirality in a geometry suitable for the most effective bonding in either the major or minor DNA groove. In general, this means the template unit will impart an approximately 90° twist to the entire system.

C. DNA sequence-recognizing units (SRU—also referred to as Y in this application). These units may be any of a variety of molecular classes that have been shown to bond to certain DNA base pair sequences. The inclusion of this component is optional in the present invention, but is highly preferred in that it acts to target the DNA cleaving reagents to specific points on the DNA strand.

D. Groove-Jumping Units (GJU—also referred to as G in this application). The inclusion of a second intercalating or groove binding moiety at an appropriate point in the molecule permits the formulation of bis cleaving agents that will complex at two proximate sites in the DNA molecule and cleave the DNA backbone at locations slightly displaced from each other. If the two cleavage sites are displaced from each other by four or six base pairs and if these two cleavage sites are at complementary DNA sugar-phosphate chains, then DNA fragments with "sticky ends" will be produced. Such DNA fragments may be recombined with any other DNA fragments that have the corresponding complementary "sticky ends", and thus, this type of DNA cleavage can be used to insert additional DNA base pairs into the middle of a DNA molecule. The most efficient strategy for achieving this goal is for the two ends of the bis cleaving agent to be tethered by a GJU so that the two cleaving units will become complexed with the DNA molecule and cause cleavage in two adjacent grooves. This type of cleavage will ensure an overlap of complementary ends of the two cleaved DNA chains of four to six base pair units, or the requisite number of overlaps to provide a fragment with "sticky ends". In essence, when the DNA cleaving system of the present invention incorporates a GJU, that reagent constitutes an artificial restriction endonuclease. Examples of suitable GJU's include salts of linear polyamines including spermine and spermidine and cyclic polyamines, such as 1,4,8,12-tetraazacyclopentadecane and 1,4,8,11-tetraazacyclotetradecane, which are capable of binding to the phosphate backbone of DNA.

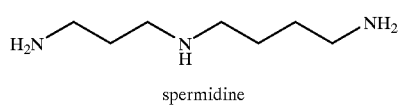

spermidine

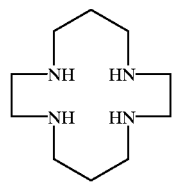

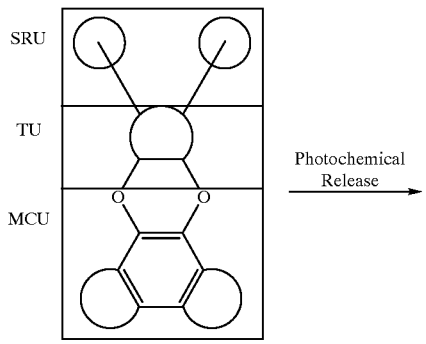

Photochemical Release →

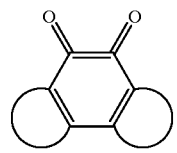

ortho-quinone
or 1,2-dicarbonyl

The individual components used in formulating the DNA cleaving reagents of the present invention are discussed in detail below.

Masked Cleaving Unit

The masked cleaving unit (the moiety designated as A or MCU in this application) is, in general terms, a 1,4-dihydrodioxin moiety capable of intercalation between DNA base pairs or binding within the DNA grooves. These moieties generally have a planar structure and do not include substituents at positions which would block their association with the DNA molecule. In the present invention, the masked cleaving units tend to be derived from ortho-quinone compounds. Examples of masked cleaving units which can be utilized in the compounds of the present invention include 1,4-dihydrodioxins derived from phenanthrenequinones, acenaphthenequinones, steroid-quinones, CC-1065 quinone analogs, and imidazole or thiazole analogs of these CC-1065 quinones. Particularly preferred masked cleaving units for use in the present invention are the 1,4-dihydrodioxins derived from phenanthrenequinones. The basic structures for these moieties are given below.

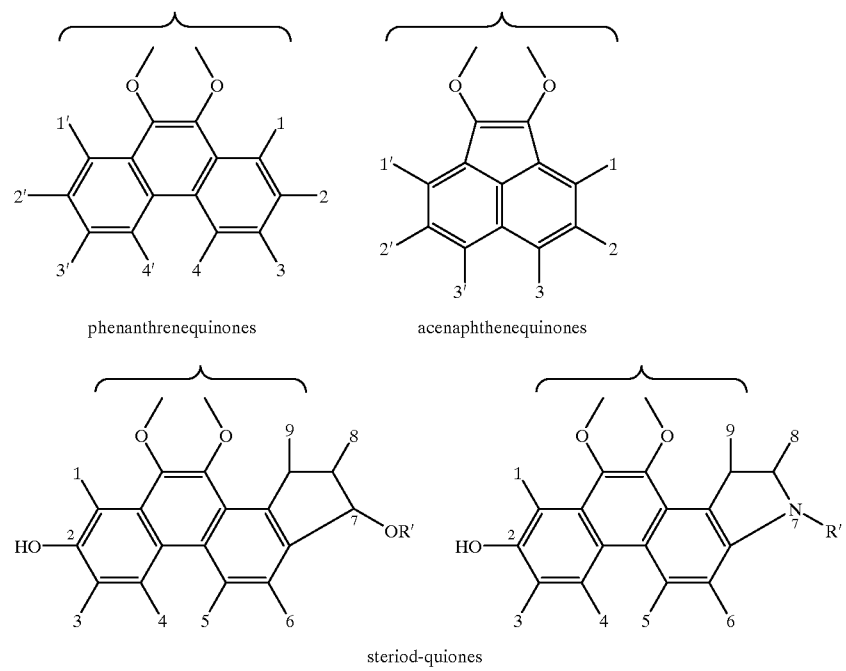

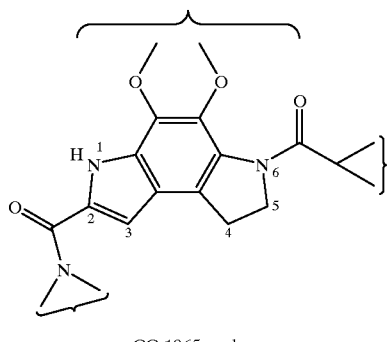 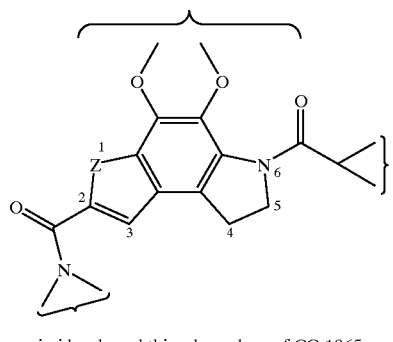

CC-1065 analogs  
X = CH or N imidazole and thiazole analogs of CC-1065  
Z = NH or S The masked cleaving units utilized in the present invention may be substituted or unsubstituted. Substituents may be placed on these masked cleaving units in order to modify their properties. For example, depending upon the nature and the location of the substituents, the intercalating and groove binding capabilities and the water solubility of the molecule can be modified. In general, when dealing with the phenanthrenequinone and acenaphthenequinone derived compounds care must be taken when placing substituents at the 3, 3', 4 and 4' positions since substituents, and particularly bulky substituents, at those positions can interfere with intercalation or association (complexation) with the DNA molecule. Substituents at the 1, 1', 2 and 2' positions can be active. For example, the placement of —$NH_2$ groups at the 2 and 2' positions enhances intercalation.

In the case of the steroid quinones, substituents in the 3–6 positions would inhibit intercalation or association, whereas substituents might be readily attached at the 1 and 2 and the 7–9 positions, and these are preferred.

CC-1065 is made from the trimerization of the units shown above where the carbonyl group at position 6 is the carbonyl group attached to the 2-position of another identical, adjacent molecule. This type of agent does not intercalate, but inserts into the DNA minor groove. Therefore, positions 1, 2, 5 and 6 are suitable for the attachment of substituents and heteroatoms, while positions 3 and 4 are only suitable for the incorporation of heteroatoms, but not substituents.

The steroid-quinone compounds, described above, provide an additional site (R') where DNA sequence-recognition units can be attached. The various analogs of CC-1065 represent an important ring modification since they tend to mimic the DNA binding situation found in the anti-tumor agent CC-1065. In this structure, multiple units could be linked together to form oligomers that will bind to the minor groove of DNA, permitting several quinone units to be unmasked in the same region of a DNA molecule.

The following is a list of substituents which may be used on the masked cleavage unit moiety of the present invention. The substituents may be used in any possible combination (where R=$CH_3$ or $CH_2CH_3$) and are classified according to the atom immediately attached to the aromatic ring:

1) Carbon
   a) Alkyl groups: R
   b) Nitrile groups: —CN
   c) Aldehyde groups: —CHO
   d) Ketone groups: —COR
   e) Carboxylic acid groups: —$CO_2H$
   f) Ester groups: —$CO_2R$
   g) Amide groups: —$CONH_2$, —CONHR, —$CONR_2$
2) Halogens
   a) —F
   b) —Cl
   c) —Br
   d) —I
3) Oxygen
   a) Phenols: —OH
   b) Alkoxy groups: —OR
   c) Carbonates: —$OCO_2R$
   d) Urethanes: —$OCONH_2$, —OCONHR, —$OCONR_2$
   e) Sulfur analogs: —OC(S)OR, —OC(O)SR, —$OCS_2R$, —OC(S)$NH_2$, —OC(S)NHR, —OC(S)$NR_2$
   f) Phosphates, their mono- and diesters: —OP(O)(OH)$_2$, —OP(O)(OH)(OR), —OP(O)(OR)$_2$
   g) Sulfates: —OS(O$_2$)OR
4) Nitrogen
   a) Amines: —$NH_2$, —NHR, —$NR_2$
   b) Amides: —NHCOR
   c) Imides: —N(C(O)R)$_2$
   d) Urethanes: —NHC(O)OR
   e) Ureas: —NHC(O)$NH_2$, —NHC(O)NHR, —NHC(O)$NR_2$
   f) Sulfur analogs: —NHC(S)R, —NHC(S)OR, —NHC(O)SR, —NHC(S)SR, —NHC(S)$NH_2$, —NHC(S)NHR, —NHC(S)$NR_2$
   g) Sulfonamides: —NHS(O$_2$)R
   h) Phosphonamides: —NHP(O)(OR)$_2$
   i) Nitro: —$NO_2$ Preferred MCU substituents include the following groups: nitrites, ketones, carboxylic acids, esters, amides, fluoride, chloride, and nitro.

Template Units

The template units utilized in the present invention are generally derived from olefins. These olefins have incorporated into their structures sites for the attachment of sequence-recognizing units or groove-jumping units. In general, template units are derived from olefins that have at least one, and as many as four aromatic substituents. The template units not only act to connect the cleaving unit to the sequence-recognizing units, but also acts to mask the cleaving unit until it has become attached to the DNA molecule. This permits a very site-specific DNA cleavage reaction. The template unit may have a specific chirality in order to assure optimum molecular geometry and alignment of the sequence-recognizing units to achieve optimum location and performance of the compounds of the present invention. In addition, because of the importance of this chirality, different enantiomers of the same compound may perform differently in the DNA cleavage reaction. In those cases, separation and use of specific enantiomers may improve DNA cleavage performance.

The compounds of the present invention have the following equivalent formulas, with the template unit being indicated by the dotted lines.

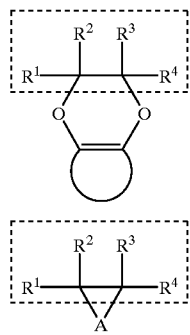

In this formula, $R^1$, $R^2$, $R^3$ and $R^4$ represent substituents the nature of which can significantly alter the performance of the compounds of the present invention. $R^1$, $R^2$, $R^3$ and $R^4$ are each selected from phenyl, substituted phenyl, $C_5$–$C_{20}$ aryl (such as biphenyl, naphthyl, phenanthryl or anthryl groups), $C_1$–$C_{20}$ alkyl, $C_1$–$C_{20}$ substituted alkyl (such as alkoxy, amino or acyl), $C_4$–$C_8$ heterocyclic rings (such as pyridyl, anthronyl, xanthonyl, thioxanthonyl, imidazole, oxazole or thiazole groups) and polypyrroles. At least one of those groups should be aromatic, and is preferably substituted phenyl or $C_4$–$C_8$ heterocyclic rings, particularly substituted phenyl. It is also preferred that at least two adjacent R groups on the template unit (for example, $R_1$ and $R^2$ or $R^3$ and $R^4$) contain aromatic moieties, such as substituted phenyl groups. One such substituted phenyl group has the formula:

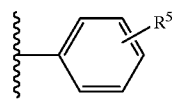

In this formula $R^5$ is selected from the group consisting of carboxylic acid groups, ester groups, phenol groups, alkoxy groups, sulfur analogs, phosphate groups including their mono- and diesters, sulfate groups, amine groups, amide groups, imide groups, urethane groups, urea groups, sulfonamide groups, phosphonamide groups and, particularly, —O—Y, —NH—Y, —$CO_2$—Y, and —C(O)NH—Y, wherein Y represents a DNA sequence-recognizing unit (discussed later in this application). In this formula, it is particularly preferred that the $R^5$ group be located at the meta-position of the ring if $R^5$ is electron-withdrawing. The meta-position provides the best site for attachment of an SRU, since from this position the SRU is directed at DNA binding sites along the floor of the groove. The para-position of one of the phenyl rings provides the best site for the attachment of an SRU via an electron-donating group since this will electronically facilitate the quinone release, or a GJU, since from this position the GJU is directed at the phosphate ridge and, hence, towards an adjacent groove in the DNA surface.

Depending on how the $R^1$–$R^4$ and $R^5$ moieties are selected and combined, the compounds of the present invention can be formulated to be water soluble. This permits the use of very low concentrations of cleaving reagent while retaining effective DNA cleaving performance. For example, when $R^5$ is an amine salt, the compounds formed are very soluble in water. These amine salt side chains may be included in the molecule as is or serve as spacer chains for the later attachment of SRU's. Examples of useful side chains (e.g., $R^3$ or $R^4$) include the following:

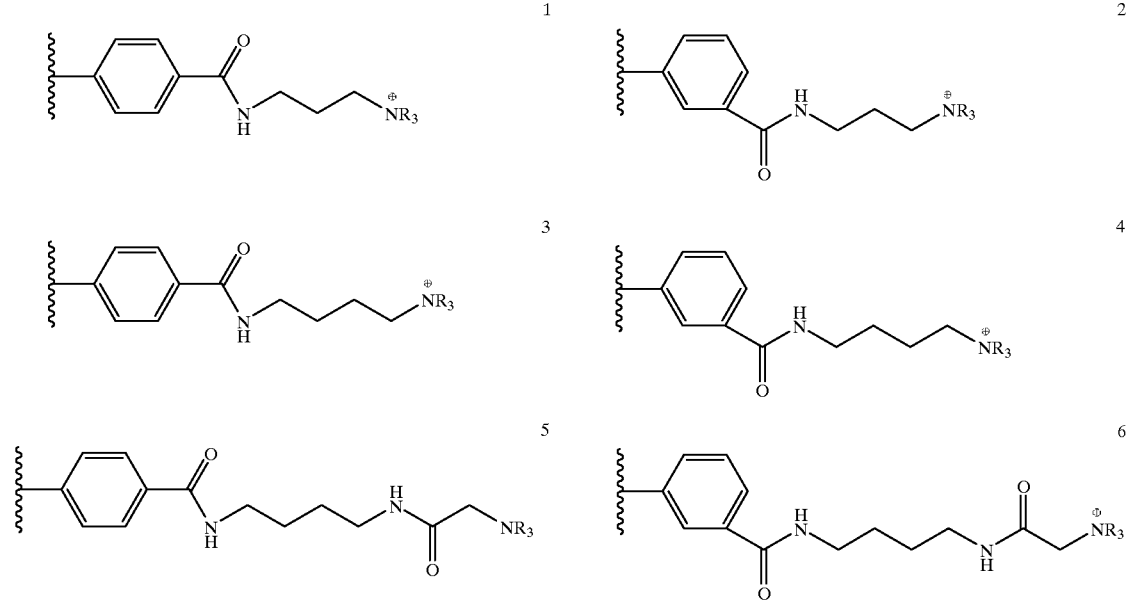

-continued

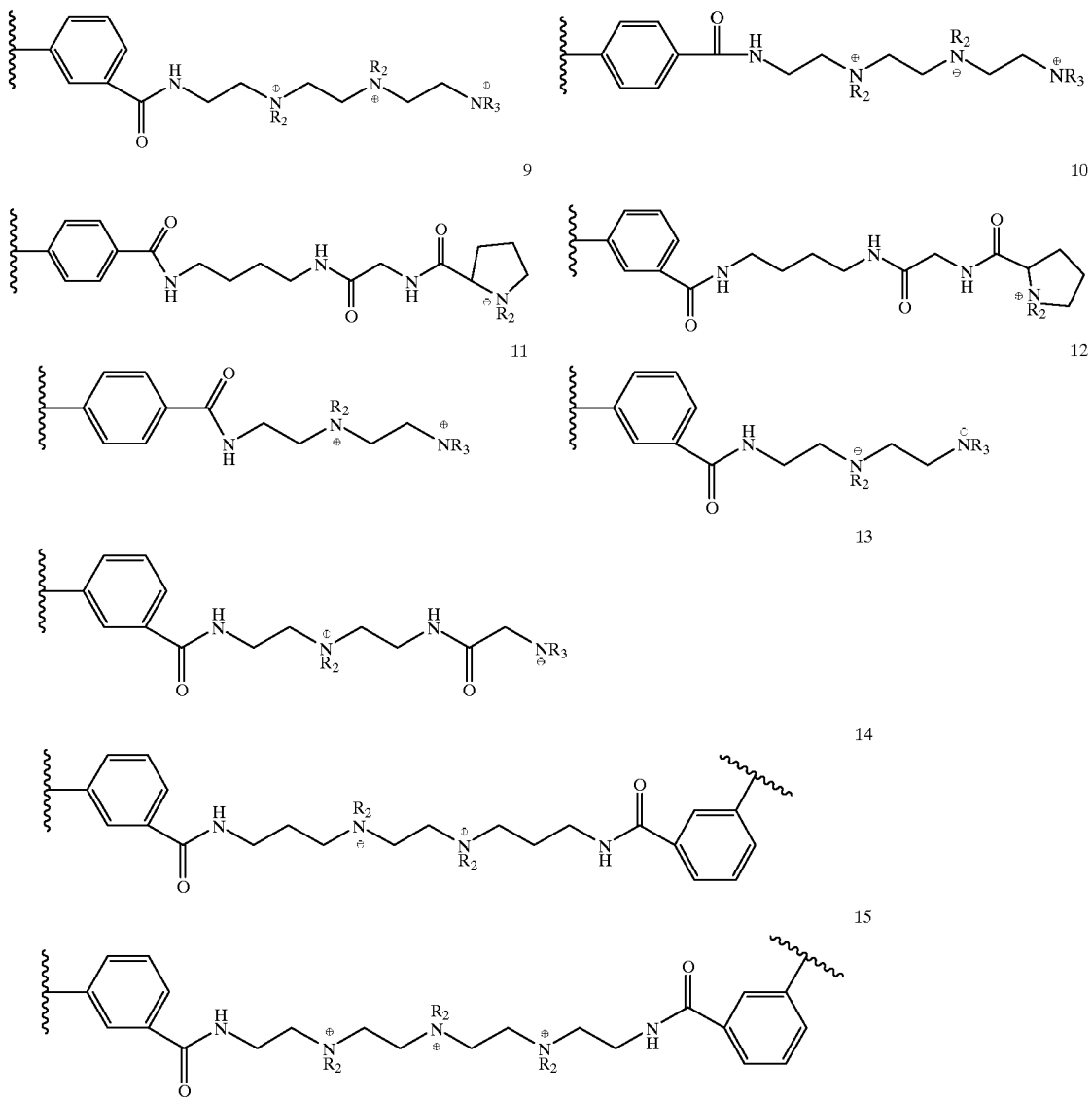

wherein R is H or $C_1$–$C_4$ alkyl, preferably methyl. Quaternary ammonium salts are preferred because they enhance the lipophilicity of the molecule and transport across cell membranes.

These chains may, for example, be terminated by any of the common amino acids such as glycine, alanine, valine, leucine, methionine, proline, phenylalanine, tryptophan, asparagine, glutamine, serine, threonine, aspartic acid, glutamic acid, tyrosine, cysteine, lysine, arginine, and histidine.

Any biologically compatible anion may be used for forming these salts. Preferred anions include chloride and carboxylates (such as citrates, acetates, phosphates and sulfates). A general scheme for synthesizing these amine salt reagents is outlined below. In the family of reagents containing electron withdrawing groups, meta substitution tends to result in more effective DNA cleavage. In reagents containing electron donating groups, the para isomers tend to provide more efficient DNA cleavage. Greater number of charges in the amine side chain also tends to provide more efficient DNA cleavage.

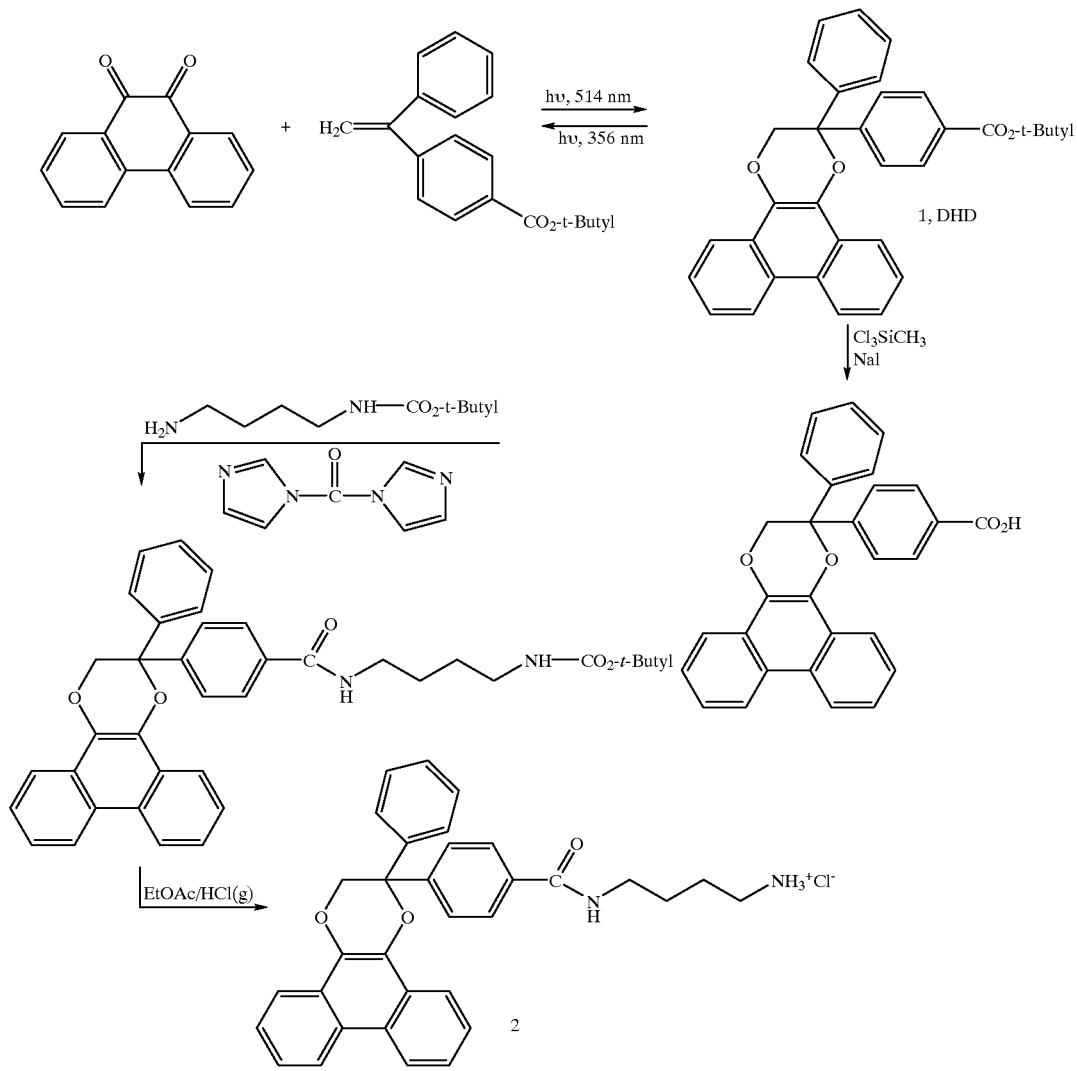

Another group of useful reagents of the present invention include those where the side chains on the template unit connect to a nucleotide, such as deoxyuridine. Examples of nucleotides which may be used include deoxyuridine, deoxyadenosine, deoxyguanosine, deoxythymidine, and deoxycytidine, with deoxyuridine being preferred. The nucleotide is attached to the reagent at a position on the nucleotide which is outwardly directed (into the groove) and away from the DNA molecule. In preferred compounds, the reagent is attached to the nucleotide at the 5-position. These compounds can be utilized in several ways. For example, they could be incorporated directly into the DNA of a living organism. This would make it possible to selectively cleave the DNA in the vicinity of the modified sites. These compounds could also be used as a base component in the synthesis of single-stranded DNA. If this synthetic DNA were designed to complex with double stranded DNA to form site-specific triple helix segments, specific DNA sites could be targeted for cleavage. By way of example, the 5-deoxyuridine derivative could be synthesized as follows:

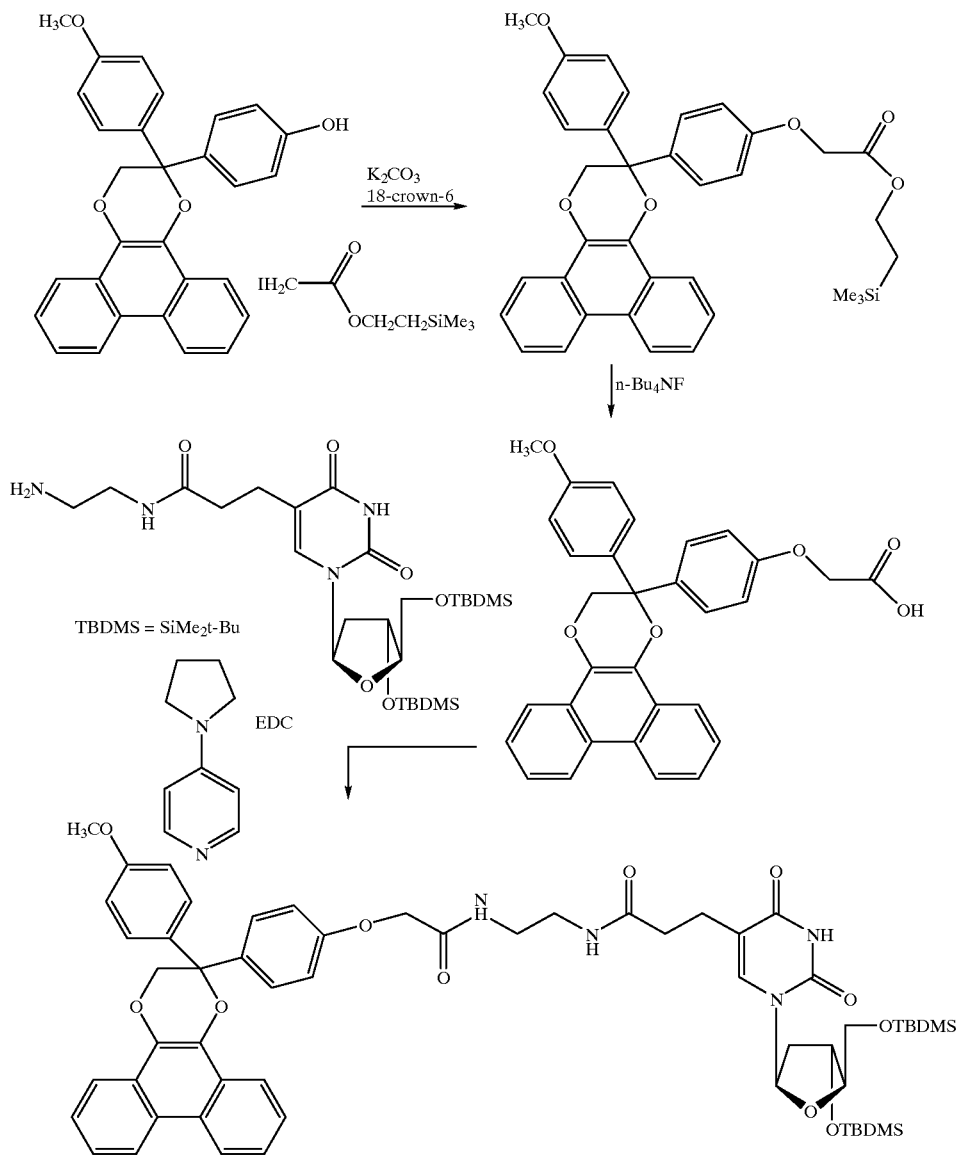

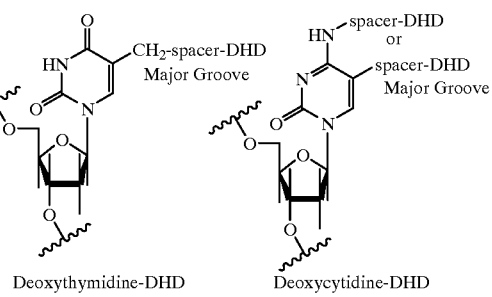

Deoxythymidine-DHD    Deoxycytidine-DHD

In these preferred nucleotide derivatives, $R^5$ is a spacer group selected from the group consisting of $C_3$ to $C_{20}$ carboxylic acid groups, ester groups, phenol groups, alkoxy groups, sulfur analogs, phosphate groups including their mono- and diesters, sulfate groups, amine groups, amide groups, imide groups, urethane groups, urea groups, sulfonamide groups and phosphonamide groups (particularly $C_3$ to $C_{20}$ amine groups) which are linked to a nucleotide selected from the group consisting of deoxyuridine, deoxyadenosine, deoxyguanosine, deoxythymidine, or deoxycytidine (particularly deoxyuridine).

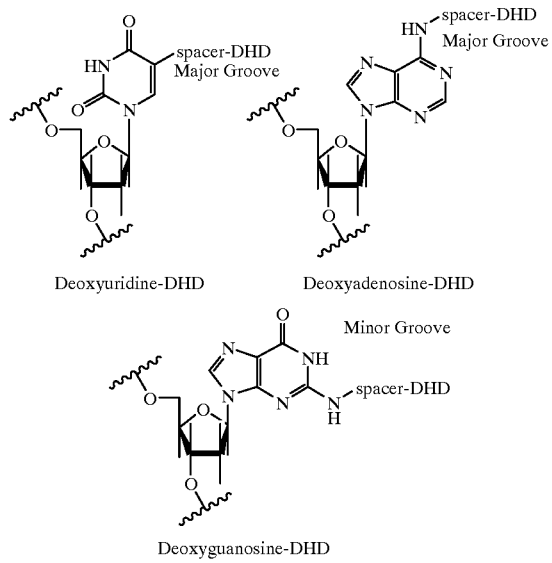

Deoxyuridine-DHD  Deoxyadenosine-DHD

Deoxyguanosine-DHD

If the template unit of a compound contains two phenyl groups and both phenyl groups are to be substituted, then only one of them is appropriately situated for attachment of an SRU, since it is resting along the groove wall, while the other phenyl group is appropriately situated for the attachment of a GJU, since it is projecting towards the phosphate ridge between the grooves. Thus, if two SRU's or two GJU's are attached each to a different phenyl group, only one will be used effectively, since the phenyl groups are in such different environments within the groove. On the other hand, if one phenyl group is substituted with an SRU in the meta-position and the other phenyl group with a GJU in the para-position, then the different environments of the two phenyl groups could be effectively exploited to construct bis cleaving reagents. This is illustrated by the following formula:

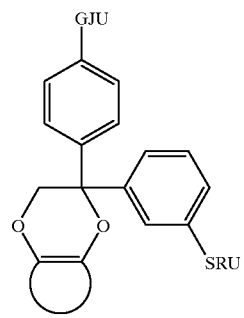

The phenyl groups, discussed above, may be replaced with heterocyclic analogs, such as the imidazoles shown below. In a system such as this, internal hydrogen bonding might be expected to orient the two substituents and their associated chains more rigidly with respect to each other.

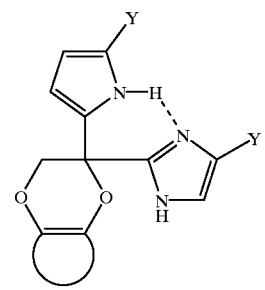

Rather than having separate substituents for the $R^3$ and $R^4$ groups in the template unit, it is also possible to combine both of those groups into a single substituent. This may be particularly useful in designing certain types of molecules. For example, in the preceeding illustrations, the templates are all chiral and, thus, only one enantiomer would fit appropriately into the chiral environment of the DNA groove. In most of those structures, the appended chains cannot interact effectively with each other. Since this interchain interaction may be essential for effective DNA sequence-recognition in certain cases, templates may be designed in which the sequence-recognizing chains can interact with each other in a chiral fashion. This type of interaction is essential, for example, in the case of a peptide SRU in which two α-helices must coil around each other in order to serve as an effective SRU. This technique would also be useful in the case of polypyrroles which must become aligned side by side in the DNA minor groove in order to become effective SRU's. The following examples demonstrate instances where $R^3$ and $R^4$ can be combined into a single substituent which allows for the chiral interaction of the attached SRU's.

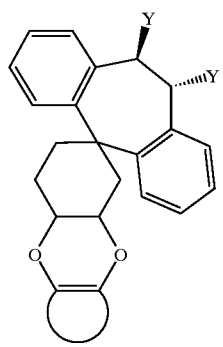 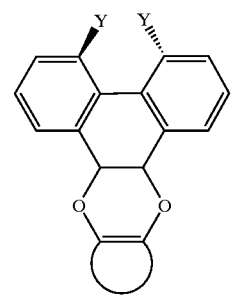

As an alternative to attaching an SRU on the template unit, as described above, it is also possible to attach the SRU directly to the masked quinone (i.e., the masked cleaving unit). In that configuration, when the quinone is released it will remain attached to the SRU. This prevents the quinone from wandering once it has been photochemically released. The result is to focus DNA cleavage to the targeted site of quinone release and to limit random DNA cleavage. An example of such a compound is made as follows.

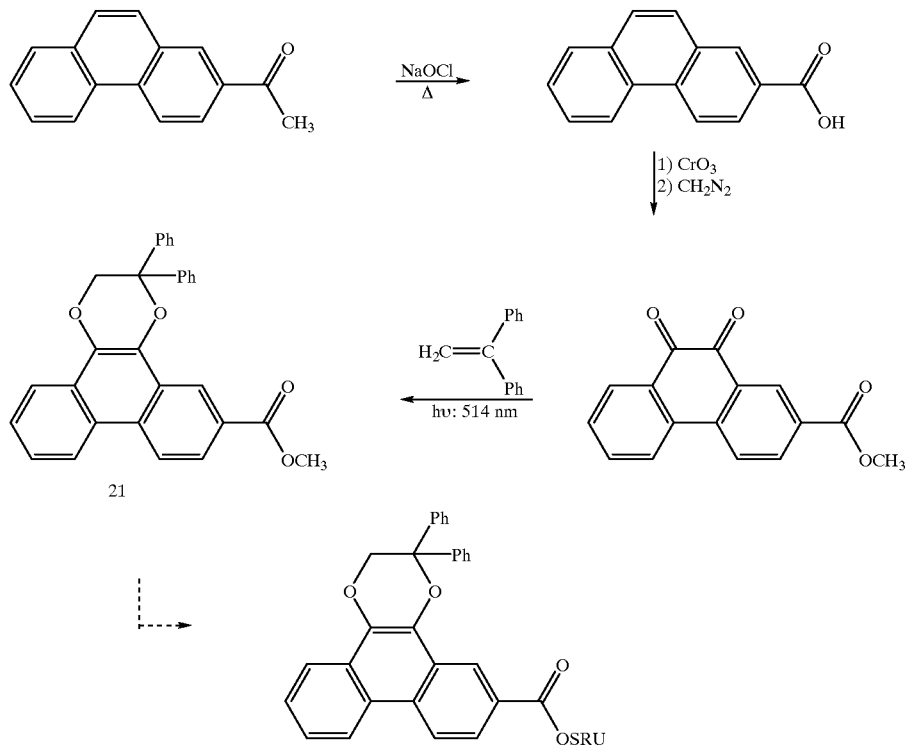

These compounds can be generally represented by the following formula, where Y is a sequence recognizing unit as defined in the present application. Attachment at the 1,1', 2 or 2' positions is preferred.

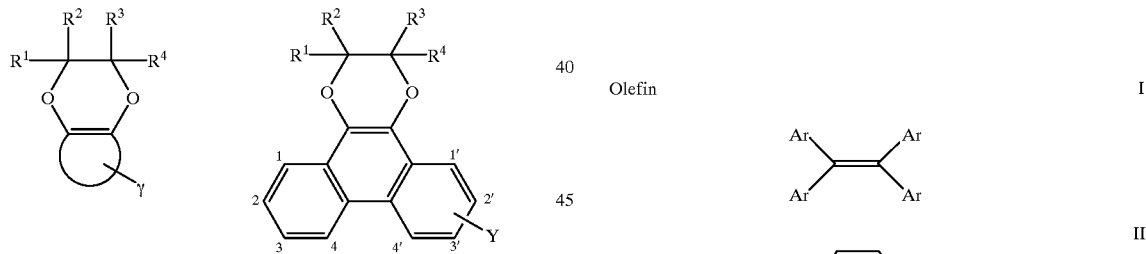

The synthesis strategy outlined above can be easily modified to synthesize reagents with sites for the attachment of two, rather than one, SRU. One SRU could be attached to the quinone moiety and the second SRU could be attached to the template unit. In order for this type of molecule to function effectively, the two SRU's would have to be directed along the DNA groove in opposite directions from the reagent, their origin point. This type of structure provides greater flexibility since it permits the use of two smaller SRU's to achieve the effect provided by a single large SRU.

A partial list of olefins useful in synthesizing the DNA cleaving reagents of the present invention and the compounds they provide are set forth in the following table. In this table, the olefin and its corresponding cleaving reagent have the same number.

21
-continued
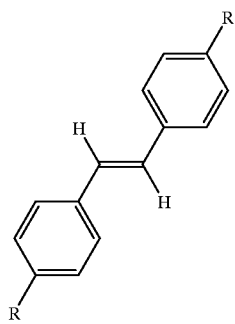
IV
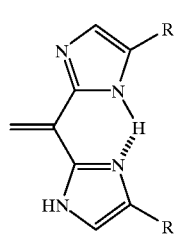
V
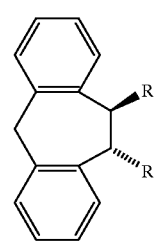
VI
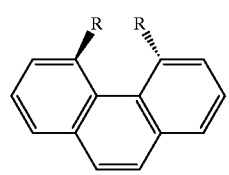
VII
DNA Cleaving Agent
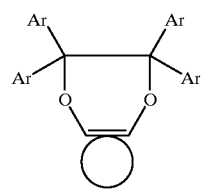
I
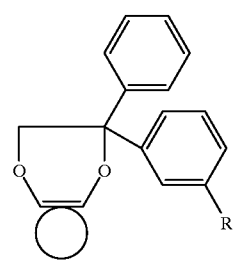
II
22
-continued
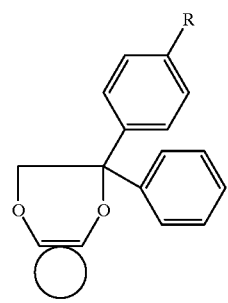
III
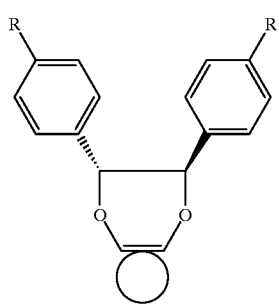
IV
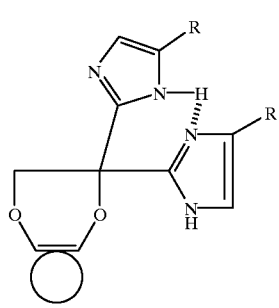
V
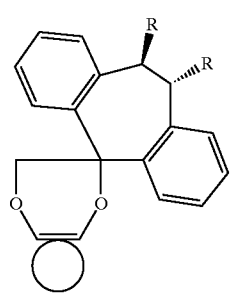
VI
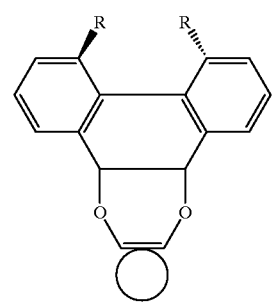
VII The basic compound of the present invention (i.e., the masked quinone) is formed by a photochemical reaction using visible light. In order to react the 1,2-quinone or 1,2-diketone material with the desired olefin, it is necessary to use visible light so as to preferentially excite only the quinone or diketone material. If the appropriate wavelength of light is not used (e.g., if UV light is utilized) the masking of the quinone will not be retained in the final molecule. In general, the 1,2-quinone or 1,2-diketone material will absorb light in the visible wavelength region ranging from about 400 to about 800 nm. It is preferred that the olefin material not absorb in this region where the 1,2-quinone or 1,2-diketone material absorbs. The product of this reaction, the 1,4-dihydrodioxin, is also photolabile, although those compounds absorb in the 200–400 nm region. The photochemistry of the 1,4-dihydrodioxins is the reverse reaction of its formation, resulting in the starting 1,2-quinone or 1,2-diketone material and the olefin. Therefore, so as not to destroy the 1,4-dihydrodioxins as they are formed, it is necessary that the synthesis light be of sufficiently long wavelength to excite only the 1,2-quinone or the 1,2-diketone, but too long a wavelength to be absorbed by both the olefin starting material and the 1,4-dihydrodioxin product.

In general, these photo-addition reactions are performed with either of the following light sources depending upon the absorption characteristics of the starting quinone: (a) the visible output of an argon ion laser at 514 nm (2–12 watts), or (b) a Rayonet Photochemical Reactor using 425, 450 nm bulbs. In the case of the laser reactions, the reaction vessel is placed in a water bath to maintain the temperature at about 20–25° C., although a temperature of 4° C. is maintained for some of the more sensitive 1,4-dihydrodioxins. The irradiation is done under an inert atmosphere (nitrogen or argon) and the reacting solution (1,2-quinone or 1,2-diketone material plus olefin material) is sparged with argon for one hour prior to irradiation. The initial concentration of the 1,2-quinone or 1,2-diketone material is approximately 0.01M in benzene or various mixtures of benzene and acetonitrile in order to dissolve some of the less soluble quinones. Any solvent with non-abstractable hydrogens or with no hydrogens at all may be used. The amount of olefin used in these reactions is about a 1:1 molar ratio relative to the 1,2-quinone or 1,2-diketone material.

Sequence-Recognizing Unit (SRU)

Although the sequence-recognizing unit (SRU, also referred to as Y in the present application) is an optional moiety in the compounds of the present invention, it is usefully included in order to target the DNA cleaving reagents to specific sites in the DNA molecule where the cleaving reaction will take place. Molecules which seek out and bind to specific DNA sequences are well known in the art. They are generally described in *Nucleic Acid Targeted Drug Design*, Propst, C. L., Perun, T. J., Eds.; Marcel Dekker, Inc.; New York, 1992, and *Antisense RNA and DNA*, Murry, J. A. H. Ed., Wiley-Liss, New York, 1992, both incorporated herein by reference. These art-known sequence recognizing units may be attached to and incorporated into the compounds of the present invention using standard biochemical techniques. Examples of SRU's and the types of molecules used to implement various targeting strategies are set forth below. All of the references cited are incorporated herein by reference.

A. Deoxyribonucleosides can participate in the formation of Triplex (Triple Helix) DNA complexes. This strategy uses both natural and synthetic nucleic acids to bond in a Hoogsteen sense to the backside of the DNA bases projecting out of the "floor" of the DNA grooves. Examples of this technique are as follows:

Perrouault, L; Asseline, U.; Rivalle, C.; Thuong, N. T.; Bisabni, E.; Giovannangeli, C.; Le Doan, T.; Helene, C., *Nature* 1990, 344: 358.

Jones, R. J.; Swaminanthan, S.; Milligan, J. F.; Wadwani, S.; Froehler, B. C.; Matteucci, M. D., *J. Am. Chem. Soc.* 1993, 115: 9816.

Griffin, L. C.; Kiessling, L. L.; Beal, P. A.; Gillespies, P.; Dervan, P. B., *J. Am. Chem. Soc.* 1992, 114: 7976.

Koh, J. S.; Dervan, P. B., *J. Am. Chem. Soc.* 1992, 114: 1470.

Radhakrishnan, I.; de los Santos, C.; Patel, D., *J. Mol. Biol.* 1991, 221: 1403.

Strobel, S. A.; Doucette-Stamni, L. A.; Riba, L.; Housman, D. E.; Dervan, P. B., *Science* 1991, 254: 1639.

Beal, P. A.; Dervan, P. B., *Science* 1991, 254: 1360.

Povsic, T. J.; Strobel, S. A.; Dervan, P. B., *J. Am. Chem. Soc.* 1992, 114, 5934.

Kiessling, L. L.; Griffin, L. C.; Dervan, P. B., Biochemistry 1992, 31, 2829.

B. Peptide Nucleic Acids are DNA analogs in which the natural sugar phosphate backbone of DNA has been replaced by a synthetic peptide backbone. The synthetic peptide nucleic acids can form triple helices with natural DNA via Hoogsteen binding in much the same fashion as natural DNA. This technique is described in Hyrup, B., Egholm, M., Nielsen, P. E., Wittrung, P., Norden, B., Buchardt, O., *J. Am. Chem. Soc.* 1994, 116: 7964.

Other hybrid DNA analogs incorporating modified sugar-phosphate backbones have been used successfully in bonding to DNA and RNA. These include DNA analogs with $C_3$ linkages, phosphorothiate linkages, nonionic methylphosphonate linkages and DNA analogs with steroid and hydrocarbon substituents to enhance transport across membranes and increase their stability to degradation. See *Antisense Strategies*, Baserga, R.; Denhardt, D. T., Eds., Annals of New York Academy of Sciences, 1992, 660.

C. Peptide sequences that participate in sequence-specific bonding to DNA have been observed in a variety of natural proteins. The DNA-peptide bonding schemes used in various situations include the helix-turn-helix, helix-loop-helix, leucine zipper, and zinc fingers. Examples of this approach are described in:

Ranganathan, D.; Patel, B. K.; Mishra, R. K., *J. Am. Chem. Soc. Chem. Commun.* 1994, 107.

Morii, T.; Simomura, M; Morimoto, S.; Saito, I., *J. Am. Chem. Soc.* 1993, 115:1150.

Hehlgans, T.; Stolz, M.; Klauser, S.; Cui, T.; Salgam, P.; Verca, S. B.; Widmann, M.; Leiser, A.; Staedler, K.; Gutte, B., *FEBS Letters* 1993, 315: 51.

D. Carbohydrates have been found to bond with sequence specificity to DNA. The primary example of this type of bonding is the anti-tumor antibiotic Calicheamicin $\gamma^1 1$. This approach is described in:

Drak, J.; Iwasawa, N.; Danishefsky, S.; Crothers, D. M., *Proc. Natl. Acad. Sci. USA* 1991, 88: 7464.

Li, T.; Zeng, Z.; Estevez, V. A.; Baldenius, K. U.; Nicolaou, K. C.; Joyce, G. F., *J. Am. Chem. Soc.* 1994, 116: 3709.

E. Tri-and polypyrrole peptides, as well as their imidazole and thiazole analogs and related synthetic variants, exhibit sequence-specific binding to DNA. In the case of tripyrroles, this is achieved via an unusual side-by-side dimer that forms in the minor groove of the DNA. This approach is described in the following references:

Bailly, C.; Houssin, R.; Bernier, J. -L, *Tetrahedron* 1988, 44: 5833.

Mrksich, M.; Dervan, P. B., *J. Am. Chem. Soc.* 1993, 115: 2572.

Dwyer, T. J.; Geierstanger, B. H.; Mrksich, M.; Dervan, P. B.; Wemmer, D. E., *J. Am. Chem. Soc.* 1993, 115: 9900.

Mrksich, M.; Dervan, P. B., *J. Am. Chem. Soc.* 1994, 116: 3663.

Mrksich, M.; Dervan, P. B., *J. Am. Chem. Soc.* 1993, 115: 9892.

Dwyer, T. J.; Geierstanger, B. H.; Bathini, Y.; Lown, J. W.; Wemmer, D. E., *J. Am. Chem. Soc.* 1992, 114: 5911.

He, G. -X.; Browne, K. A.; Groppe, J. C.; Blasko, A.; Mei, H. -Y.; Bruice, T. C., *J. Am. Chem. Soc.* 1993, 115: 7061.

F. A pyrrolidinoindole, the antitumor antibiotic CC-1065, binds to the minor groove of DNA in a fashion similar to the polypyrrole, described above. These materials can be modified to form poly ortho-quinones, and thus, can serve as both SRU's and masked cleavage units. See, Daekyu, S.; Hurley, L. H., Biochemistry 1992, 31: 2822.

Groove-jumping units can also optionally be included in the compounds of the present invention. They are important is desired to displace cleavage over a palindromic segment of DNA. However, this strategy requires the synthesis of relatively large molecules. Groove-jumping requires much smaller cleaving reagents in which the ends of the terminal MCU's are linked with a GJU. Since this GJU is universal (i.e., it works in all situations), this strategy is more economical. A GJU consists of simple polyamine salts derived from diamines, triamines and polyamines, including spermidine, or spermine attached with hydrocarbon tethers of the appropriate length for the particular template units. See, Addess, K. J.; Feigon, J., *Biochemistry* 1994, 33: 12386, and Addess, K. J.; Feigon, J,. *Biochemistry,* 1994, 33: 12397. See also, Dervan and Becker, *J. Am. Chem. Soc.,* 1978, 100: 1968–1970. Examples of bis DNA cleaving reagents include:

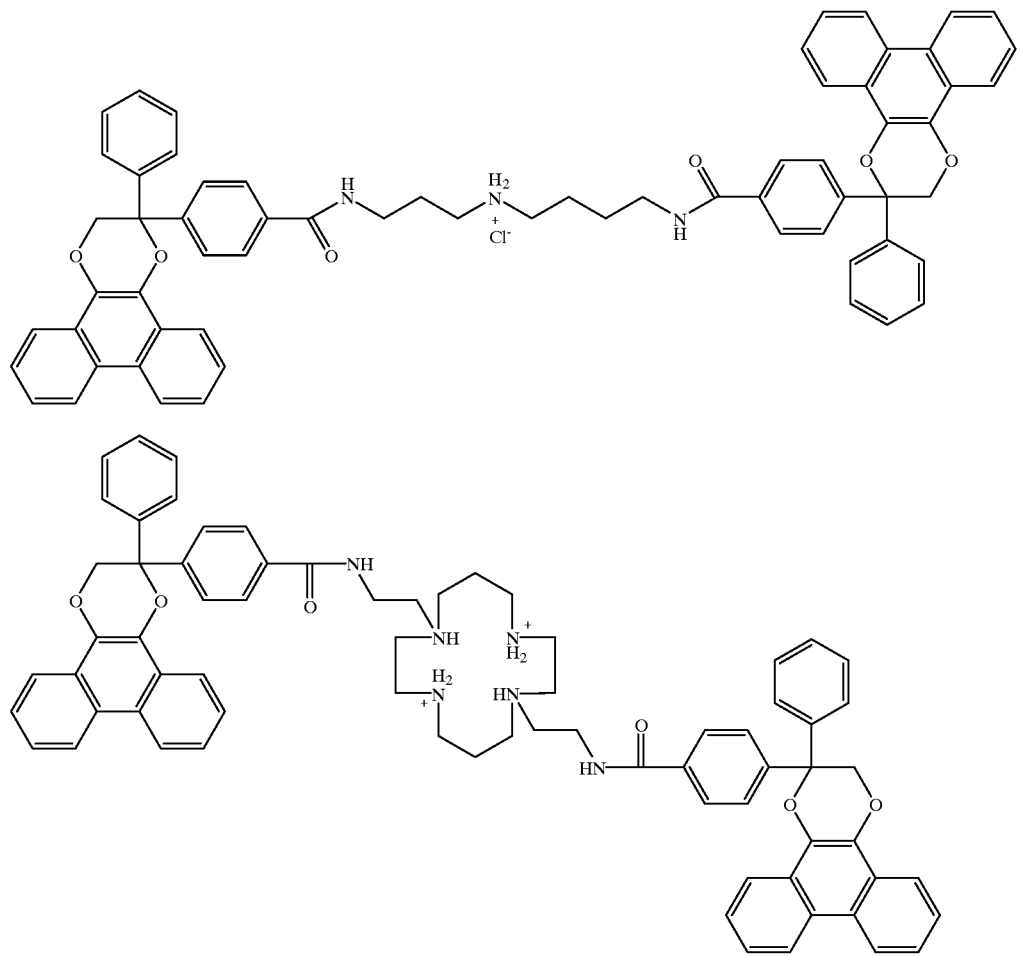

if the goal is to produce DNA fragments containing "sticky ends". Bis intercalation without groove-jumping is known in the antibiotic Triostin A. However, with Triostin A, the two sites of DNA intercalation are within the same groove and close together and, in order to produce "sticky ends", the two intercalation sites (and hence the cleaving sites) should be displaced by at least four base pairs. Two strategies exist for achieving this end: 1) groove-following, and 2) groove-jumping. Groove-following might be advantageous when it Particularly preferred compounds of the present invention include the following phenanthrenequinone compounds wherein $R^5$ is selected from carboxylic acid groups, ester groups, amide groups, phenol groups, alkoxy groups, urethane groups, sulfur analogs, phosphate groups including their mono- and diesters, sulfate groups, amine groups, imide groups, urea groups, sulfonamide groups, phosphonamide groups, and particularly —O—Y, —NH—Y, —CO$_2$—Y, and —C(O)NH—Y, wherein Y is a sequence-recognizing unit. Especially preferred compounds are ones where $R^5$ is located in the meta or para positions and is selected from

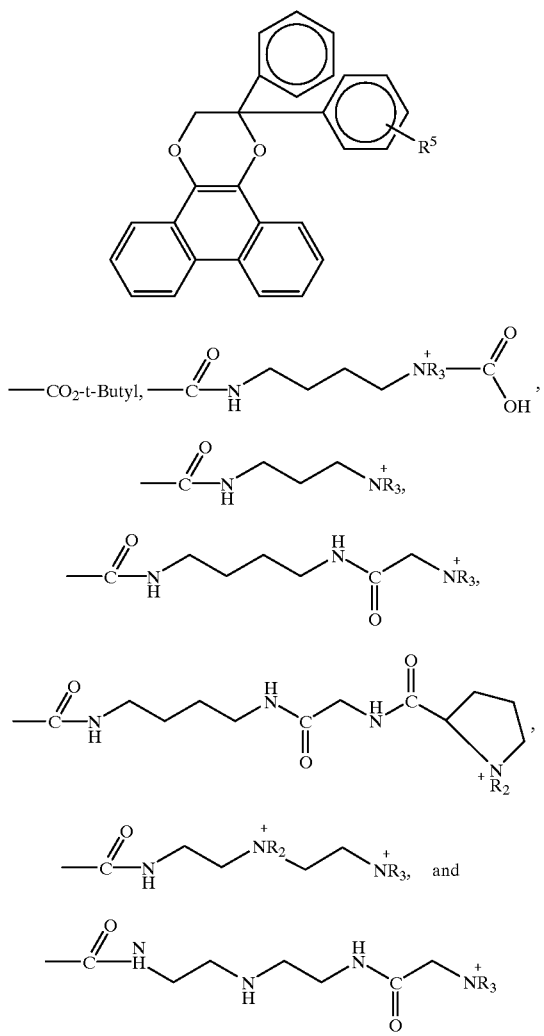

wherein R is H or $C_1$–$C_4$ alkyl, preferably methyl.

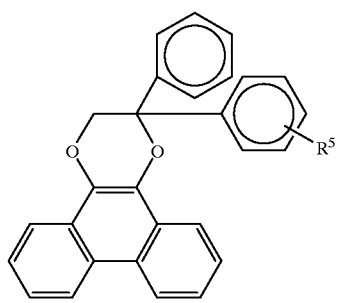

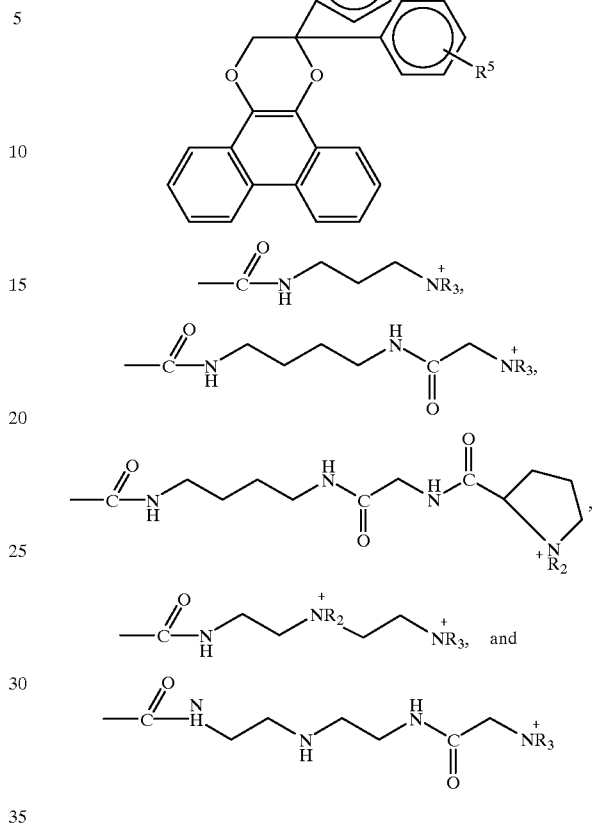

Also preferred are reagents where a sequence recognizing unit (Y) is attached to these $R^5$ moieties. There are several reasons for using this structure, i.e., one in which a spacer chain is attached between the basic reagent structure and the SRU. The primary reason is that the spacer chains provide a flexible linkage. When the spacer chain is of the appropriate length (i.e., between about 3 and about 20 carbon, Also preferred are reagents where a sequence recognizing unit (Y) is attached to these $R^5$ moieties. There are several reasons for using this structure, i.e., one in which a spacer chain is attached between the basic reagent structure and the SRU. The primary reason is that the spacer chains provide a flexible linkage. When the spacer chain is of the appropriate length (i.e., between about 3 and about 20 carbon, nitrogen or oxygen atoms in any combination), it will extend from the site of attachment on the reagent, which may be projecting out of the DNA groove, back into the groove to near the groove floor where the DNA sequence can be recognized by the SRU through backside bonding to the partially exposed bases in the groove floor. Without the spacer chain the SRU would project out of the groove and be much less effective in its sequence recognizing role. An additional function of the spacer chain is to provide sites for the incorporation of positively charged ammonium ions. These ammonium ions make the reagents water soluble. Furthermore, the positive ammonium ions are electrostatically attracted to the negative phosphate ions lining the DNA grooves. This attraction tends to draw the spacer chain down into the groove where it is guided along the middle of the groove by the rows of phosphates on either side. This electrostatic chain guide provides the optimum orientation for the SRU which will continue down the groove and "read" the base sequence information from the floor of the groove.

Other preferred DNA cleaving reagents of the present invention include the following.

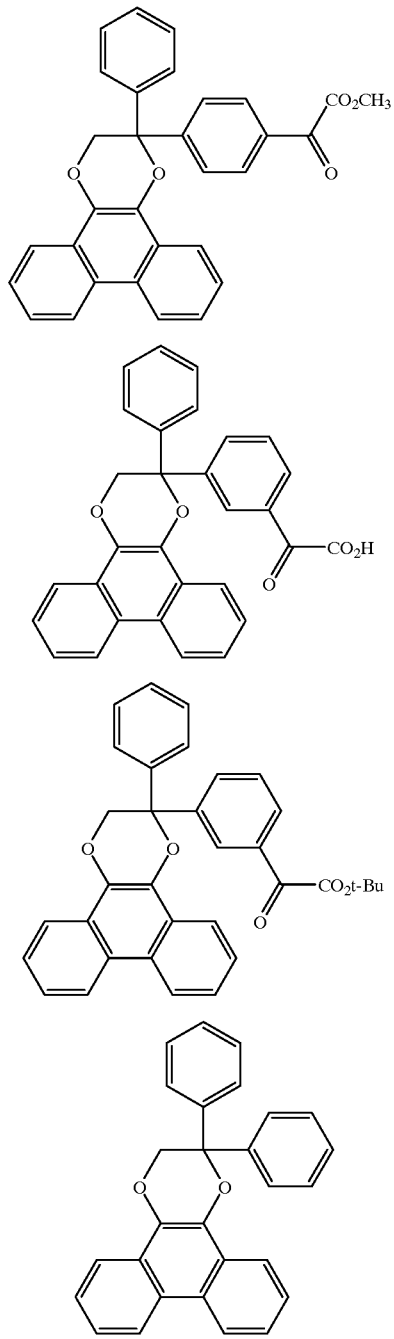

-continued

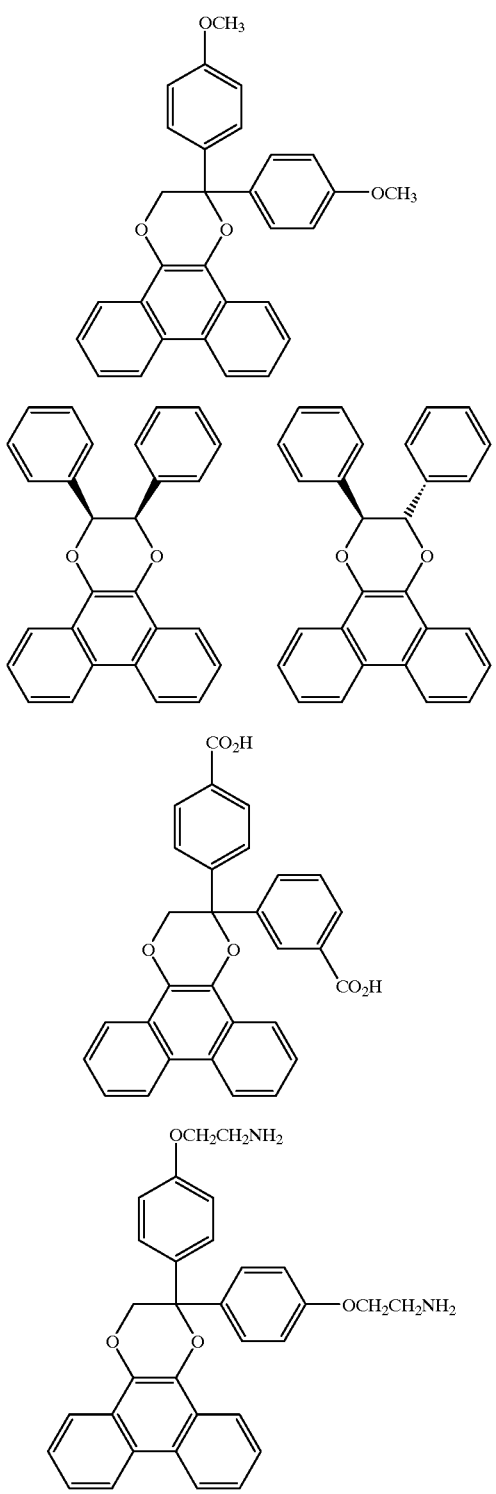

-continued

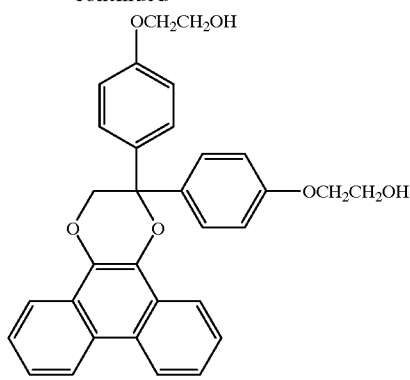

The present invention also emcompasses pharmaceutical compositions which comprise a pharmaceutically safe and effective amount of the DNA cleaving reagents of the present invention together with a pharmaceutical carrier. The precise dosage of reagent administered will depend upon the severity and nature of the particular condition being treated, the duration of treatment, the adjunct therapy used, the age and physical condition of the patient, and like factors within the specific knowledge and expertise of the attending physician. The dosage selected must be consistent with a sound benefit/risk ratio for the patient. The pharmaceutical compositions of the present invention could be used, for example, to treat cancer, especially localized tumors, or to target and destroy pathogens in the blood supply. Generally, the compositions will contain from about 0.01% to about 1% of the reagent component. The compositions may be administered by any conventional manner, including intravenously, parenterally or orally, and may be compounded in conventional formulations, such as solutions, capsules, tablets or granules.

As used herein, the term "pharmaceutical carrier" denotes a solid or liquid filler, diluent or encapsulating substance. Some examples of the substances which can serve as pharmaceutical carriers include sugars, such as lactose, glucose and sucrose; starches, such as corn starch and potato starch; cellulose and its derivatives, such as sodium carboxymethyl cellulose, ethyl cellulose, and cellulose acetate; powdered tragacanth; malt; gelatin; talc; stearic acid; magnesium stearate; calcium sulfate; vegatable oils, such as peanut oil, cottonseed oil, sesame oil, olive oil, corn oil and oil of theobroma; polyols, such as propylene glycol, glycerin, sorbitol, mannitol and polyethylene glycol; agar; alginic acid; pyrogen-free water; isotonic saline; and phosphate buffer solutions, as well as non-toxic compatible substances used in pharmaceutical formulations. Wetting agents and lubricants, such as sodium lauryl sulfate, as well as coloring agents, flavoring agents, tableting agents and preservatives, can also be present. Formulation is done using conventional techniques.

The pharmaceutical carriers employed in the compositions of the present invention are used at concentrations sufficient to provide a practical size to dosage relationship. Preferably, the pharmaceutical carrier comprises from about 50% to about 99.9% of the total composition.

DNA Cleavage Reaction

The present invention also encompasses the reaction by which the DNA cleaving reagents of the present invention are reacted with DNA molecules in the presence of ultraviolet light to cleave the DNA. In general, the reaction is carried out by forming a solution, preferably an aqueous solution, of the DNA cleaving reagent of the present invention, having a concentration of no greater than about 1M, preferably from about 1 μM to about 1 M, most preferably from about 10 μM to about 200 μM, most preferably from about 30 μM to about 200 μM. This solution is mixed with the DNA (covalently closed supercoiled DNA) which is sought to be cleaved. The DNA is generally present in a solution wherein the solvent is Tris-HCl, pH=7.4 or another solvent of neutral pH, the DNA having a concentration of from about 1 to about 100 μM in base pairs, preferably from about 40 to about 50 μM in base pairs. The two solutions are then mixed together at a temperature of from about 20 to about 37° C., preferably from about 20 to about 25° C., and at a pH of from about 6.9 to about 8.5. If the pH needs to be adjusted conventional buffers, such as Tris-HC1, may be added. The combined solution is then irradiated with light having a wavelength of from about 333 to about 550 nm, preferably from about 333 to about 500 nm, more preferably from about 333 to about 400 nm, with an intensity of from about 5 to about 19 mwatts/cm², preferably from about 10 to about 19 mwatts/cm², for a period of from about 10 seconds to about 30 minutes, preferably from about 10 seconds to about 5 minutes, more preferably from about 30 seconds to about 2 minutes. The DNA fragments formed may be isolated using conventional biochemical techniques. Using a similar procedure, the reagents of the present invention can be used to cleave RNA.

Although not critical for the reaction, the mixed solution of DNA cleaving reagent and DNA may be allowed to incubate for a period of time prior to irradiation with the UV light. This incubation can last for from about 0 minutes to about 48 hours. The reaction may take place either in the presence or in the absence of oxygen. However, cleavage rates may be accelerated by the presence of molecular oxygen. In a 100% oxygen atmosphere complete destruction of the DNA can be realized under conditions where, without oxygen, only nicking or single strand breaks are observed. Thus, controlling the oxygen content of the reaction is important depending upon the extent and placement of the DNA cleavage required.

Although not wishing to be bound by theory, it is believed that when the DNA and the DNA cleaving reagent are mixed together in solution, the sequence recognizing portion of the reagent molecule locates itself at the appropriate sequence of the DNA molecule and the masked cleaving unit portion of the molecule is then oriented to intercalate between base pairs of the DNA or bind within the grooves of the DNA. This forms a complex between the DNA molecule and the DNA cleaving reagent. When this complex is irradiated with UV light, the reagent of the present invention is fragmented to form phenanthrenequinone or its analogs. It is this quinone that reacts with the DNA via either a hydrogen abstraction or electron transfer mechanism, leading to the cleavage of the DNA.

The following non-limiting examples are intended to illustrate the compounds and complexes of the present invention, as well as the process for cleaving DNA utilizing those compounds.

EXAMPLE I

A DNA cleaving reagent of the present invention is synthesized as follows.

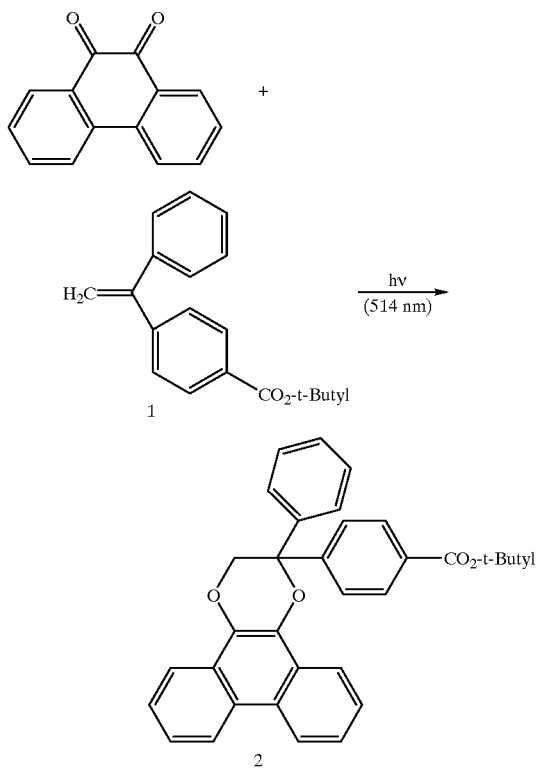

Experimental Procedure

To a solution of the phenanthrenequinone (0.1400 g, $6.73 \times 10^{-4}$ moles) in 70 mL $C_6H_6$ ($9.6 \times 10^{-3}$ M) is added the olefin (0.1885 g, $6.73 \times 10^{-4}$ moles) and this solution is sparged with argon for one hour. At this point, the solution is irradiated for 4 h, in a water bath at room temperature, with the visible output of an argon ion laser (514 nm, 8.2 W, with the laser output dispersed through a lens). The reaction is monitored for the appearance of product by TLC (40% $CH_2Cl_2$/hexane, 3 elutions). The benzene is evaporated to dryness under reduced pressure to produce the crude reaction mixture as a red oil. This red oil is purified by chromatography on 80 g of finer than 200 mesh silica gel eluting with 40% $CH_2Cl_2$/hexane to yield the 1,4-dihydrodioxin as a cream colored solid (0.1400 g, 42.6%, mp 119–122° C.).

Spectral data $^1$H NMR (300 MHz, $CDCl_3$, all peaks reported relative to TMS): δ 1.51 (s, 9H), 4.81, (dd, 2H), 7.5 (m, 7H), 7.9 (d, 2H), 8.1 (d, 1H), 8.5 (m, 3H). $^{13}$C NMR (300 MHz, $CDCl_3$, all peaks reported relative to TMS): δ 28.2, 70.1, 79.7, 81.1, 120.7, 120.9, 122.5, 122.7, 125.1, 126.7, 126.8, 126.9, 126.95, 128.3, 128.4, 128.7, 129.7, 131.8, 132.3, 140.6, 145.4, 165.6. UV ($CH_2Cl_2$), nm ε reported in parentheses: 300 (11,057), 313 (10,411), 351 (1393), 369 (1479); HRMS: calcd. for $C_{33}H_{28}O_4$, calcd 488.1951, obsd. 488.1971

EXAMPLE II

A DNA cleaving reagent of the present invention is synthesized as follows.

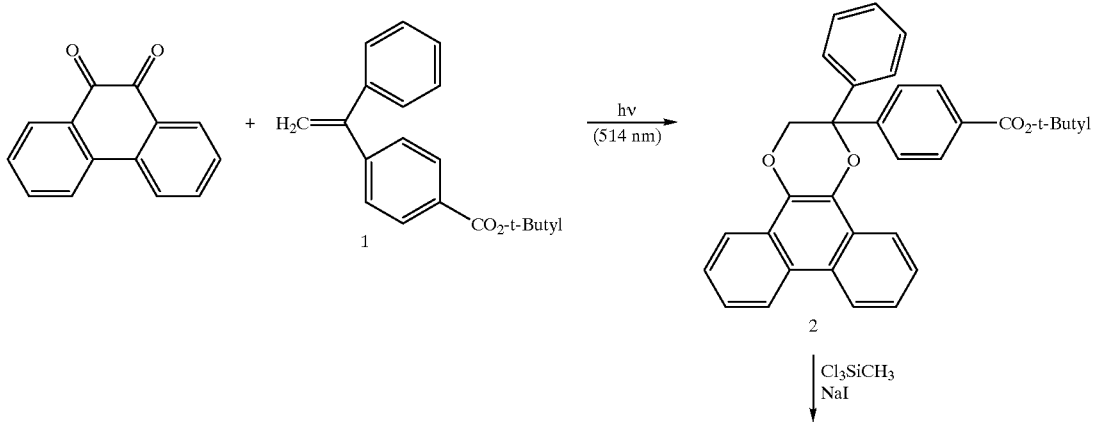

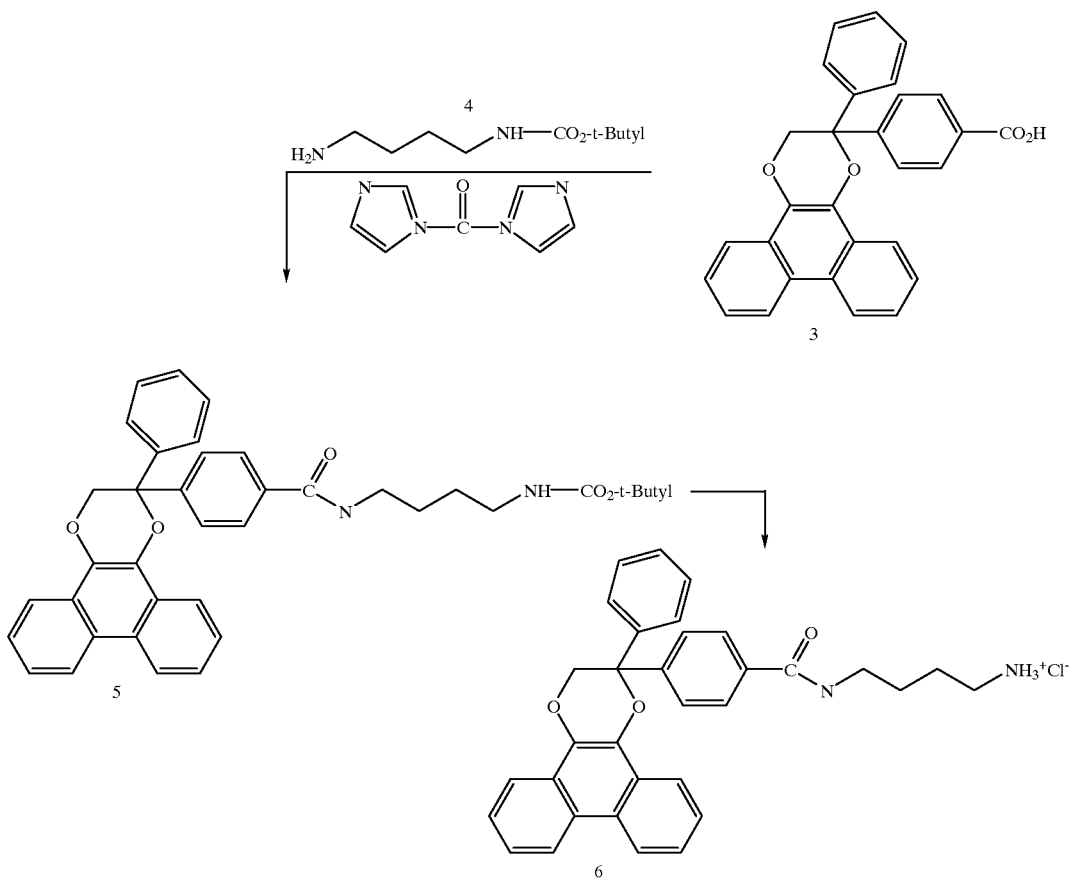

The olefin 1 and the mono-BOC protected amine 4 are prepared by standard literature methods. See Ohta, S., Shimabayashi, A., Aono, M., *Synthesis* (1982) 833, and Krapcho, A. P., Kuell, C. S., *Syn. Commun.* (1990) 20:2559.

Preparation of 1,4-dihydrodioxin 2

As described in Example I.

Preparation of 3

In a flame-dried, 3-neck flask under Ar is placed NaI (0.0538 g, 3.59×10$^{-4}$ moles, oven-dried, 24 h, 120° C.) dissolved in 10 mL of dry acetonitrile. To this is added compound 2 (0.1400 g, 2.87×10$^{-4}$ moles) in 10 mL of dry acetonitrile. The Cl$_3$SiCH$_3$ (34 μL, 2.89×10$^{-4}$ moles) is added next. The solution becomes yellow and a precipitate forms. This reaction is stirred for 5 h at room temperature under Ar. At this time, the reaction mixture is poured into 50 mL of ice water and extracted with Et$_2$O (50 mL). The organic phase is washed with 10% Na$_2$S$_2$O$_3$ (3×25 mL) followed by 10% NaOH (3×25 mL). The aqueous phase is acidified at 0° C. with conc. HCl (aq), and back extracted with Et$_2$O (3×30 mL). The organic phase is washed with satd. NaCl, dried over MgSO$_4$ and evaporated to dryness to produce the acid 3 as a colorless solid (0.1000 g, 81% yield, mp 138–142° C.).

Spectral Data $^1$H NMR (300 MHz, CDCl$_3$, all peaks reported relavite to TMS): δ 4.88 (dd, 2H), 7.57 (cm, 14H), 8.1 (m, 3H), 8.61 (m, 3H); UV (CH$_2$Cl$_2$), nm, ε reported in parentheses: 300 (6467), 312 (8947), 350 (1431), 368 (1521); HRMS: calcd. for C$_{29}$H$_{20}$O$_4$, calcd 432.1325, obsd. 432.1391.

Preparation of 5

In a flame-dried, 3-neck flask under Ar is placed the acid 3 (0.1000 g, 2.32×10$^{-4}$ moles) in 5 mL of CH$_2$Cl$_2$. To this solution is added carbonyldiimidazole (0.0375 g, 2.32×10$^{-4}$ moles) at which point CO$_2$ evolution is observed. The reaction mixture is stirred for 1 h at room temperature under Ar before the mono-BOC protected amine 4 (0.0500 g, 2.66×10$^{-4}$ moles) in 5 mL CH$_2$Cl$_2$ is added to the reaction mixture. This mixture is stirred for 36 h at room temperature under Ar during which time the solution becomes cloudy with precipitate forming. The reaction mixture is then diluted with CH$_2$Cl$_2$ (15 mL), washed with 5% NaOH (3× 15 mL) followed by satd. NaCl (3×15 mL); the organic phase is dried over MgSO$_4$ and evaporated to dryness to yield the crude reaction product as a cream colored solid. This crude material is purified by chromatography on 70 g of finer than 200 mesh silica gel eluting with 40% ethyl acetate-60% hexanes to produce the t-BOC amide 5 as a colorless solid (0.0867 g, 62% yield, mp 126–130° C).

Spectral Data $^1$H NMR (300 MHz, CDCl$_3$, all peaks reported relative to TMS): δ 1.40 (s, 9H), 1.46 (bs, 4H), 3.0 (d, 2H), 3.3 (d, 2H), 4.6 (bs, 1H), 4.9 (dd, 2H), 6.4 (bs, 1H), 7.5 (cm, 9H), 8.1 (d, 1H), 8.5 (m, 3H); $^{13}$C NMR (26 MHz, CDCl$_3$, all peaks reported relative to TMS): 11.7, 20.1, 24.1, 25.1, 25.9, 29.2, 37.1, 67.6, 77.2, 118.2, 118.5, 120.0, 120.2, 122.7, 123.6, 124.2, 124.3, 124.35, 124.4, 124.5, 124.6, 124.77, 124.95, 126.2, 129.8, 130.6, 132.04, 138.15, 141.6, 153.8, 164.8; UV (CH$_2$Cl$_2$), nm, ε reported in parentheses: 302 (5786), 314 (9170), 352 (1409), 369 (1484); HRMS: M$^+$ C$_{38}$H$_{38}$N$_2$O$_5$, fragment obsd. C$_{20}$H$_{22}$N$_2$O$_3$, calcd. 338.1603, obsd. 338.1624.

Preparation of 6

The t-BOC amide 5 (0.0500 g, 8.31×10$^{-5}$ moles) is dissolved in 3 mL ethyl acetate and cooled to 0° C. To this solution is added 15 mL of a HCl(g) saturated solution of ethyl acetate. This reaction mixture is stirred at 0° C. and monitored every ½ h by TLC (70% ethyl acetate-30% hexanes) for the disappearance of starting material. After 4 h at 0° C., no starting material is evident by TLC and the reaction mixture becomes cloudy. The ethyl acetate solution is subsequently concentrated to 5 mL and precipitate immediately forms (no heat applied to the solution). Fresh ethyl acetate is added to the reaction mixture and this solution evaporated again to about 5 mL. This process is repeated until the reaction mixture shows no trace of acid (HCl) by testing with pH paper. Once all of the excess acid has been swept from the reaction mixture, the mixture is diluted with 15 mL of $Et_2O$, cooled to 0° C. and the resulting solid collected by filtration to yield the amine salt 6 (0.0421 g, 94% yield, mp 186–191° C).

Spectral Data $^1$H NMR (300 MHz, $CDCl_3$, all peaks reported relative to TMS): δ 1.17 (bs, 2H), 1.44 (bs, 2H), 2.60 (m, 8H), 4.50 (dd, 2H), 7.32 (m, 10H), 7.91 (m, 4H), 8.32 (m, 3H). UV ($CH_2Cl_2$), nm, ε reported in parentheses: 300 (6362), 310 (6802), 352 (1026), 366 (1026); IR (KBr): 3964, 3419, 3030, 2942, 1705, 1635 $cm^{-1}$.

EXAMPLE III

The following example illustrates the process of the present invention for the cleavage of DNA.

General Procedures

A measured quantity of the cleaving reagent is dissolved in ultra pure water to afford concentrations of cleaving reagent solutions ranging from 50–200 μM. A measured aliquot of the solution of cleaving agent is placed in an Eppendorf tube and to this solution is added the supercoiled RF DNA (1 μL of ΦX 174, purchased from Gibco BRL) at room temperature and buffer is then added to take the volumes of each sample up to 10 μL. Samples may be incubated at this time from 0–24 hours. Each sample is then placed on a piece of parafilm atop a metal stage at 0° C. The sample is immediately irradiated with the UV output of a Blackray lamp (356 nm, 15–18 $mW/cm^2$) for 1–2 minutes at 0° C., with the light source typically being approximately 3 inches away from the sample. Irradiations are carried out in air and no effort is made to exclude oxygen during these experiments. Once irradiated, the sample is placed in the well of an agarose gel and the gel apparatus is covered with aluminum foil to insure that the sample is not further exposed to any light. Once all samples have been irradiated and loaded into the wells of the gel, the gel is developed by electrophoresis (80 volts) for ca. 40–90 minutes, subsequently stained with ethidium bromide (3.18 μM aqueous solution) for 30 minutes and photographed on a short wave UV transilluminator using Polaroid 667 coaterless film with an orange filter at f/5.6 for 1–3 seconds.

A general stock solution of the 1,4-dihydrodioxin 6 (see Example II) is prepared by dissolving 11 mg of 6 in 1 mL of ultra pure water to make a $2.04×10^{-2}$M (or $2.04× 10^4$ μM) solution. From this general stock solution, the following two solutions of cleaving agent are prepared:

Preparation of Solutions

Solution A (100 μM); 24.5 μL of the general stock solution is diluted to 5 mL (total volume) to make 100 μM solution A (cleaving agent). This is used in study #1, gel #1. An aliquot of 5 μL of Solution A is then diluted to a total of 10 μL with ΦX 174 RF DNA (1 μL) and sodium phosphate buffer (40 mm, pH=7, 4 μL) in an Eppendorf tube and the samples are incubated for times of 5 h, 3 h, 2 h, 1 h, and 0 h prior to the 1 minute irradiation (see tables). The final concentration of the 1,4-dihydrodioxin 6 being 50 μM in each sample.

Solution B (200 μM): 49.0 μL of the general stock solution is diluted to 5 mL (total volume) to make 200 μM solution B (cleaving agent). This is used in study #2, gel #2. An aliquot of 5 μL of Solution B is then diluted to a total of 10 μL with ΦX 174 RF DNA (1 μL) and sodium phosphate buffer (4 μL) in an Eppendorf tube and the samples are incubated for times of 5 h, 3 h, 2 h, 1 h, and 0 h prior to the 1 minute irradiation (see table). The final concentration of the 1,4-dihydrodioxin 6 being 100 μM in each sample.

Method of Irradiation and Analysis

The sample incubation is conducted in the dark. Following the specified incubation time, the sample is consecutively placed on a fresh square of parafilm atop a metal stage at 0° C. (on ice), using a micropipet. The sample is then irradiated for 1 minute with a Black-ray lamp (356 nm, intensity approximately 16–18 $mW/cm^2$ at the surface of the sample), with the sample being approximately 3 inches away from the light source. After irradiation, the sample is taken up in the micropipet and injected into a well of a freshly prepared 1.5% agarose gel with a tris acetate running buffer. After all of the samples are irradiated and loaded into the gel, the gel is run at 80 volts for 90 minutes, stained with the ethidium bromide solution (3.18 μM aqueous solution for 0.5 h at room temperature), and photographed on a short wave UV transilluminator using Polaroid 667 coaterless film with an orange filter for 1.5 seconds. The relative efficiency of DNA cleavage is subsequently evaluated quantitatively by densitometry using a combination of Adobe Photoshop, Sigma Scan (Jandel Scientific) and Origins 294 software.

Study #1, gel #1 studies, summarized:

| Lane | 1 | 2 | 3 | 4 | 5 | 6 | 7 | 8 | 9 | 10 | 11 | 12 |
|---|---|---|---|---|---|---|---|---|---|---|---|---|
| DNA, uL | 1 | 1 | 1 | 1 | 1 | 1 | 1 | 1 | 1 | 1 | 1 | X |
| Solution A, uL | 5 | 5 | 5 | 5 | 5 | 5 | 5 | 5 | 5 | 5 | X | X |
| Buffer, uL | 4 | 4 | 4 | 4 | 4 | 4 | 4 | 4 | 4 | 4 | 9 | X |

Sample preparation, per lane:

1) Lane 1: incubate sample for 5 h, irradiate for 1 minute.
2) Lane 2: incubate sample for 3 h, irradiate for 1 minute.
3) Lane 3: incubate sample for 2 h, irradiate for 1 minute.
4) Lane 4: incubate sample for 1 h, irradiate for 1 minute.
5) Lane 5: incubate sample for 0 h, irradiate for 1 minute.
6) Lane 6: incubate sample for 5 h, no irradiation.
7) Lane 7: incubate sample for 3 h, no irradiation.
8) Lane 8: incubate sample for 2 h, no irradiation.
9) Lane 9: incubate sample for 1 h, no irradiation.
10) Lane 10: incubate sample for 0 h, no irradiation.
11) Lane 11: Super-coiled DNA only, no irradiation.
12) Lane 12: DNA ladder, no irradiation.

where x indicates no sample entered.

Study #2, gel #2 studies, summarized:

| Lane | 1 | 2 | 3 | 4 | 5 | 6 | 7 | 8 | 9 | 10 | 11 | 12 |
|---|---|---|---|---|---|---|---|---|---|---|---|---|
| DNA, uL | 1 | 1 | 1 | 1 | 1 | 1 | 1 | 1 | 1 | 1 | 1 | X |
| Solution B, uL | 5 | 5 | 5 | 5 | 5 | 5 | 5 | 5 | 5 | 5 | X | X |
| Buffer, uL | 4 | 4 | 4 | 4 | 4 | 4 | 4 | 4 | 4 | 4 | 9 | X |

Sample preparation, per lane:

1) Lane 1: incubate sample for 5 h, irradiate for 1 minute.
2) Lane 2: incubate sample for 3 h, irradiate for 1 minute.
3) Lane 3: incubate sample for 2 h, irradiate for 1 minute.
4) Lane 4: incubate sample for 1 h, irradiate for 1 minute.

5) Lane 5: incubate sample for 0 h, irradiate for 1 minute.

6) Lane 6: incubate sample for 5 h, no irradiation.

7) Lane 7: incubate sample for 3 h, no irradiation.

8) Lane 8: incubate sample for 2 h, no irradiation.

9) Lane 9: incubate sample for 1 h, no irradiation.

10) Lane 10: incubate sample for 0 h, no irradiation.

11) Lane 11: Super-coiled DNA only, no irradiation.

12) Lane 12: DNA ladder, no irradiation.

where x indicates no sample entered.

Results

Study #1, gel #1

In this study, the cleaving reagent is at 50 µM concentration. For samples in lanes 1, 2, 3, 4 and 5, which constitute those samples which are irradiated, cleavage of the DNA is seen as judged by the Polariod photograph of the gel. The amount of incubation time does not appear to be critical in this study and nicking of the DNA occurs with incubation times ranging from 5 h to 0 h. In lanes 6, 7, 8, 9, and 10, which represent the dark control reactions, it is found that the DNA is not nicked substantially, if at all when compared to the sample of RF DNA itself, with no cleavage reagent added, as shown in lane 11. It should be noted that in many instances, the DNA supplied by Gibco BRL contains small amounts of relaxed (nicked) DNA and this must be taken into account in interpretation of the cleaving studies. In this study, cleavage of the DNA occurs when the samples in lanes 1–5 are irradiated with UV light. This is quite evident when the amounts of super-coiled DNA are compared in the samples in lanes 1–5 and lanes 6–10. In lanes 1–5, the amount of RF super-coiled DNA is greatly diminished when compared to lanes 6–10 of this gel.

Study #2, gel #2

In this study, the cleavage reagent is at 100 µM concentration. For samples in lanes 1, 2, 3, 4, and 5, which constitute those samples which are irradiated, superior cleavage of the DNA is seen at this higher concentration as judged by the Polaroid photograph of the gel when compared to the 50 µM concentration. The amount of incubation time again does not appear to be critical in this study and nicking of the DNA occurs with incubation times ranging from 5 h to 0 h. In lanes 6, 7, 8, 9, and 10, which represent the dark control reactions, it is found that the DNA is not nicked substantially, if at all when compared to the sample of RF DNA itself, with no cleavage reagent added, as shown in lane 11. Again, it should be noted that in many instances, the DNA supplied by Gibco BRL contains small amounts of relaxed (nicked) DNA and this must be taken into account in interpretation of the cleaving studies. In this study, cleavage of the DNA occurs when the samples in lanes 1–5 are irradiated with UV light. This is quite evident when the amounts of super-coiled DNA are compared in the samples in lanes 1–5 and lanes 6–10. In lanes 1–5, the amount of RF super-coiled DNA is greatly diminished and the amount of relaxed (nicked) DNA is significantly enhanced when compared to lanes 6–10 of this gel.

What we claim is:

1. A pharmaceutical composition comprising (a) a safe and effective amount of a DNA cleaving reagent having the formula

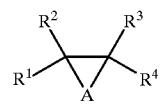

wherein A is a moiety capable of intercalation between DNA base pairs or groove binding and $R^1$, $R^2$, $R^3$ and $R^4$ are each selected from the group consisting of phenyl, substituted phenyl, $C_5$–$C_{20}$ aryl, $C_1$–$C_{20}$ alkyl, $C_1$–$C_{20}$ substituted alkyl, $C_4$–$C_8$ heterocyclic rings, and polypyrroles; at least one of said R groups being aromatic; and (b) a safe and effective amount of a pharmaceutical carrier.

2. A pharmaceutical composition according to claim 1 wherein in the DNA cleaving reagent A is a 1,4-dihydrodioxin derived from the group consisting of phenanthrenequinones, acenaphthenequinones, steroidquinones, CC-1065 quinone analogs, imidazole analogs of CC-1065 quinones, and thiazole analogs of CC-1065 quinones.

3. A pharmaceutical composition according to claim 2 wherein in the DNA cleaving reagent A is selected from the group consisting of

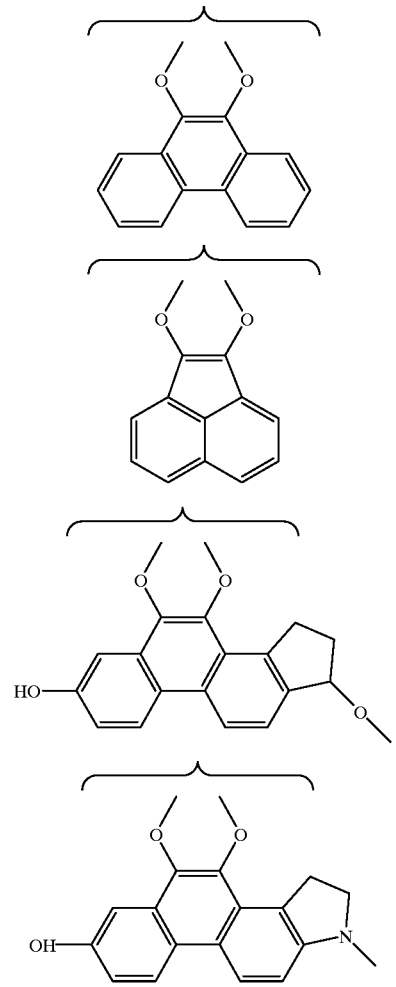

-continued

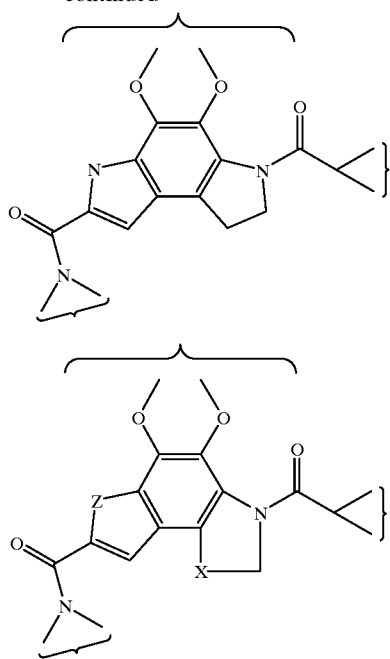

wherein X is selected from the group consisting of CH and N, and Z is selected from the group consisting of NH and S.

4. A pharmaceutical composition according to claim 3 wherein in the DNA cleaving reagent at least one of said R groups is selected from the group consisting of substituted phenyl groups and $C_4$–$C_8$ heterocyclic rings.

5. A pharmaceutical composition according to claim 4 wherein in the DNA cleaving reagent at least one of said R groups is selected from substituted phenyl groups.

6. A pharmaceutical composition according to claim 5 wherein in the DNA cleaving reagent at least two R groups pendant from the same carbon are selected from substituted phenyl groups.

7. A pharmaceutical composition according to claim 6 wherein in the DNA cleaving reagent at least one of said substituted phenyl group has the formula

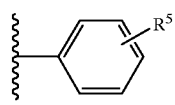

wherein $R^5$ is selected from the group consisting of carboxylic acid groups, ester groups, amide groups, phenol groups, alkoxy groups, urethane groups, sulfur analogs, phosphate groups, phosphate mono- and diesters, sulfate groups, amine groups, imide groups, urea groups, sulfonamide groups, phosphonamide groups, —O—Y, —NH—Y, —CO$_2$—Y, and —C(O) NH—Y; and Y is a DNA sequence-recognizing unit.

8. A pharmaceutical composition according to claim 7 wherein in the DNA cleaving reagent $R^5$ is located at the meta-position of the phenyl ring.

9. A pharmaceutical composition according to claim 7 wherein in the DNA cleaving reagent $R^5$ is located at the para-position of the phenyl ring.

10. A pharmaceutical composition according to claim 4 wherein in the DNA cleaving reagent A is a 1,4-dihydrodioxin derived from phenanthrenequinone.

11. A pharmaceutical composition according to claim 7 wherein in the DNA cleaving reagent A is a 1,4-dihydrodioxin derived from phenanthrenequinone.

12. A pharmaceutical composition according to claim 11 wherein the DNA cleaving reagent is substituted at any of the 1, 1', 2 or 2 positions with substituents selected from the group consisting of nitrile groups, ketone groups, carboxylic acid groups, ester groups, amide groups, nitro groups, fluoride and chloride.

13. A pharmaceutical composition according to claim 11 wherein the DNA cleaving reagent has the formula

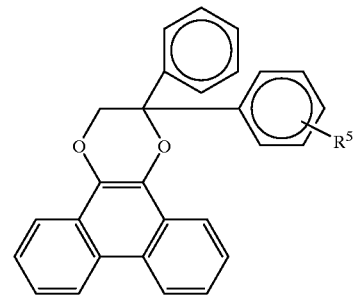

wherein $R^5$ is located in the meta or para position and is selected from the group consisting of carboxylic acid groups, ester groups, amide groups, phenol groups, alkoxy groups, urethane groups, sulfur analogs, phosphate groups, phosphate mono- and diesters, sulfate groups, amine groups, imide groups, urea groups, sulfonamide groups, phosphonamide groups, —O—Y, —NH—Y, —CO$_2$—Y, and —C(O)NH—Y, wherein Y is a sequence-recognizing unit.

14. A pharmaceutical composition according to claim 11 wherein the DNA cleaving reagent has the formula

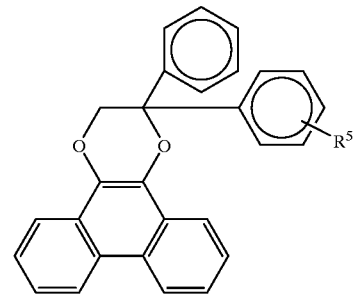

wherein $R^5$ is located in the meta or para position and is a spacer group selected from the group consisting of $C_3$ to $C_{20}$ carboxylic acid groups, ester groups, phenol groups, alkoxy groups, sulfur analogs, phosphate groups, phosphate mono- and diesters, sulfate groups, amine groups, amide groups, imide groups, urethane groups, urea groups, sulfonamide groups and phosphonamide groups, which is linked to a nucleotide selected from the group consisting of deoxyuridine, deoxyadenosine, deoxyguanosine, deoxythymidine, and deoxycytidine.

15. A pharmaceutical composition according to claim 14 wherein in the DNA cleaving reagent $R^5$ is a $C_3$ to $C_{20}$ amine group.

16. A pharmaceutical composition according to claim 15 wherein in the DNA cleaving reagent the $R^5$ spacer group is linked to deoxyuridine.

17. A pharmaceutical composition according to claim 13 wherein in the DNA cleaving reagent $R^5$ is selected from the group consisting of
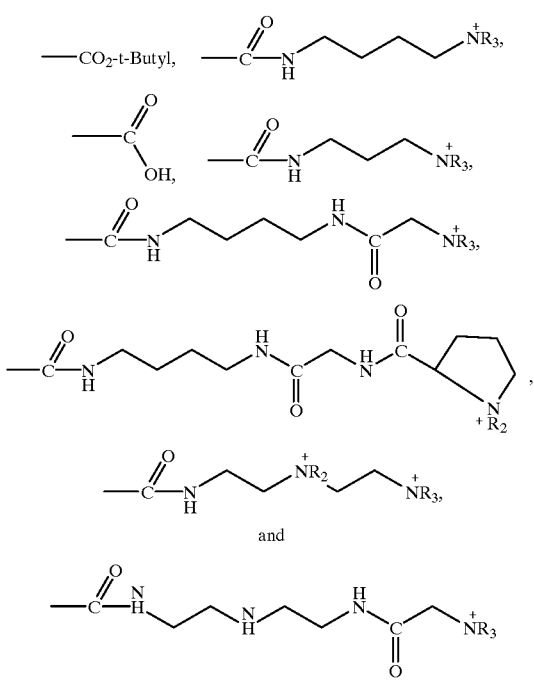
wherein R is selected from H and $C_1$–$C_4$ alkyl.
18. A pharmaceutical composition according to claim 3 wherein the DNA cleaving reagent is selected from the group consisting of
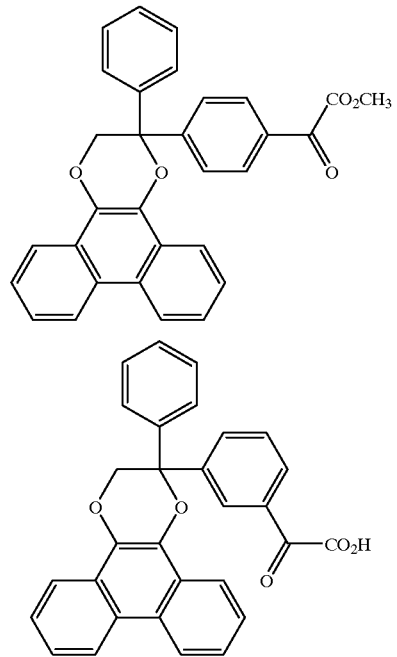
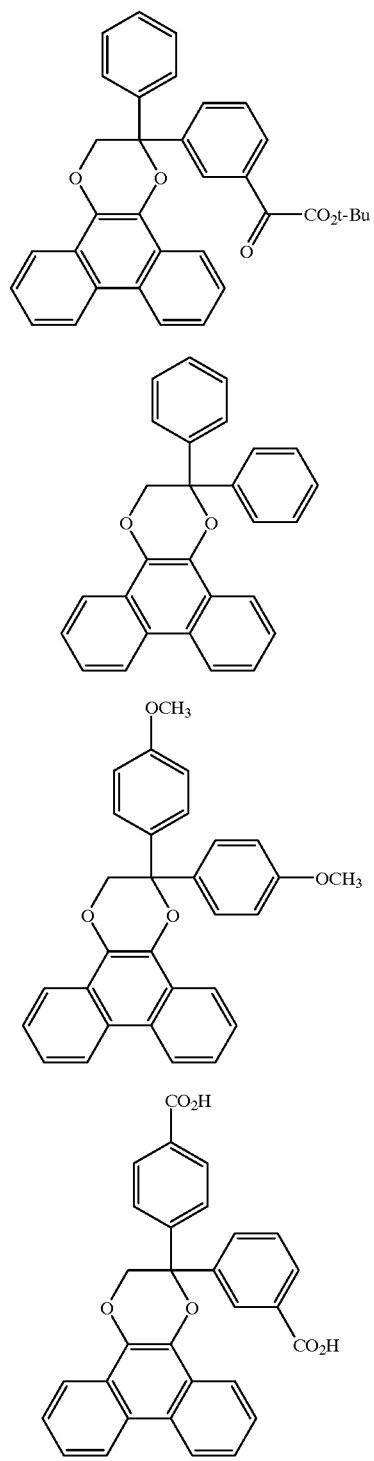

-continued

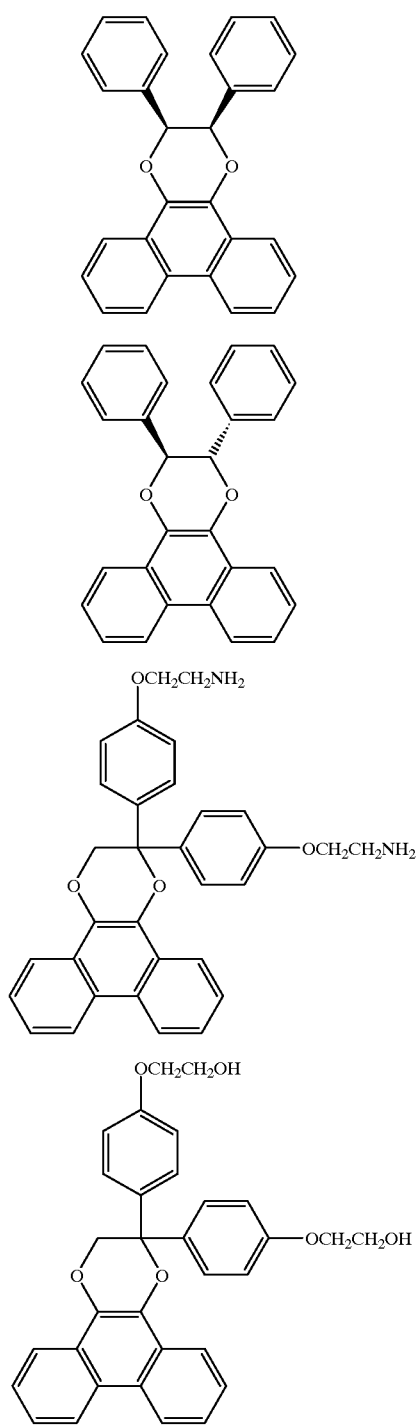

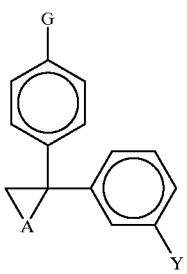

wherein Y is a DNA sequence-recognizing unit and G is a groove-jumping unit.

20. The complex between a DNA molecule and the DNA cleaving reagent having the formula

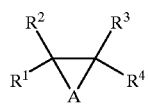

wherein A is a moiety capable of intercalation between DNA base pairs or groove binding and $R^1$, $R^2$, $R^3$ and $R^4$ are each selected from the group consisting of phenyl, substituted phenyl, $C_5$–$C_{20}$ aryl, $C_1$–$C_{20}$ alkyl, $C_1$–$C_{20}$ substituted alkyl, $C_4$–$C_8$ heterocyclic rings, and polypyrroles; at least one of said R groups being aromatic.

21. The complex according to claim 20 wherein in the DNA cleaving reagent A is selected from the group consisting of

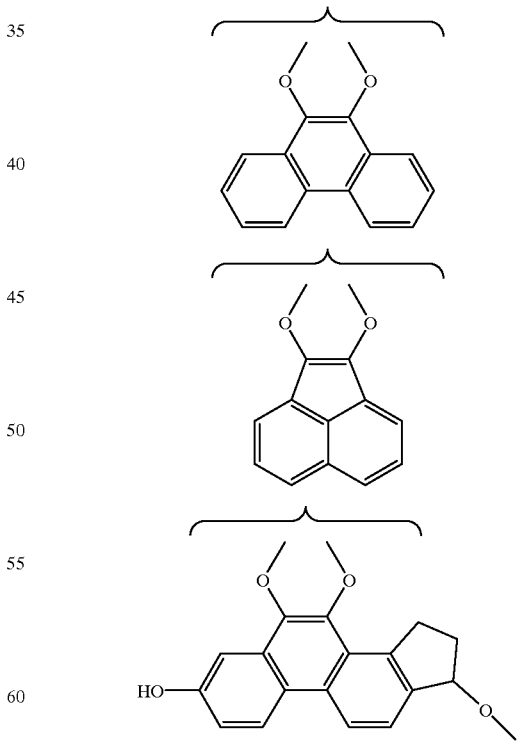

19. A pharmaceutical composition according to claim 3 wherein the DNA cleaving reagent has the formula -continued

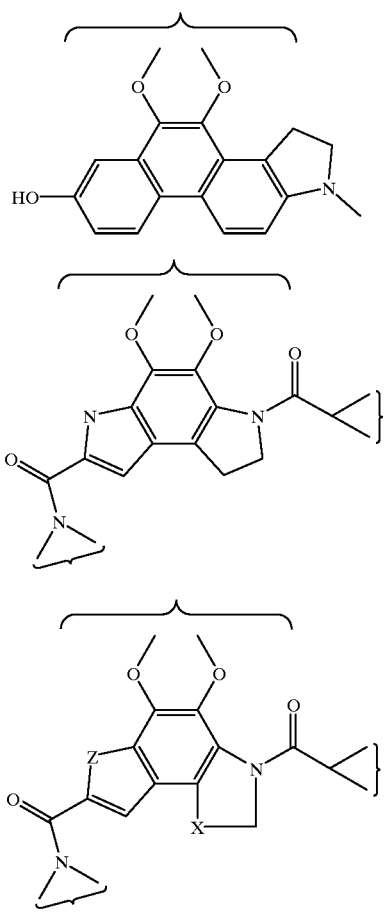

wherein X is selected from the group consisting of CH and N, and Z is selected from the group consisting of NH and S.

22. The complex according to claim 21 wherein in the DNA cleaving reagent at least one of said R groups is a substituted phenyl having the formula

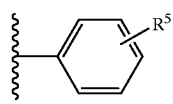

wherein $R^5$ is selected from the group consisting of carboxylic acid groups, ester groups, amide groups, phenol groups, alkoxy groups, urethane groups, sulfur analogs, phosphate groups, phosphate mono- and diesters, sulfate groups, amine groups, imide groups, urea groups, sulfonamide groups, phosphonamide groups, —O—Y, —NH—Y, —$CO_2$—Y, and —C(O) NH—Y; and Y is a DNA sequence-recognizing unit.

23. The complex according to claim 20 wherein in the DNA cleaving reagent A is a 1,4-dihydrodioxin derived from phenanthrenequinone.

24. The complex according to claim 22 wherein in the DNA cleaving reagent $R^5$ is selected from the group consisting of

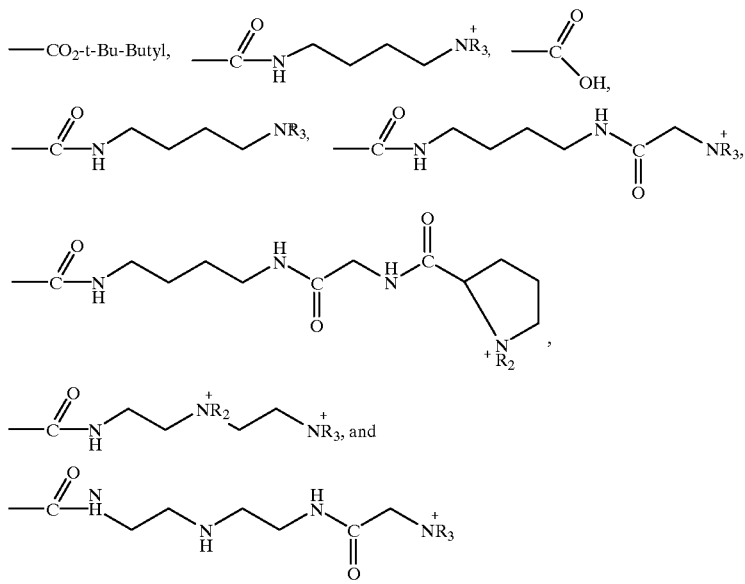

wherein R is selected from H and $C_1$–$C_4$ alkyl.

25. The complex according to claim 20 wherein the DNA cleaving reagent has the formula

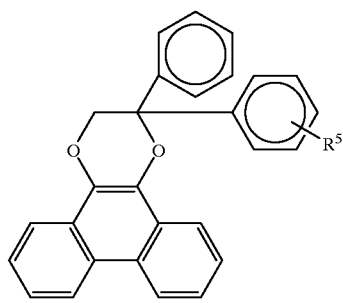

wherein $R^5$ is located in the meta or para position and is a spacer group selected from the group consisting of $C^3$–$C^{20}$ carboxylic acid groups, ester groups, phenol groups, alkoxy groups, sulfur analogs, phosphate groups, phosphate mono- and diesters, sulfate groups, amine groups, amide groups, imide groups, urethane groups, urea groups, sulfonamide groups and phosphonamide groups, which is linked to a nucleotide selected from the group consisting of deoxyuridine, deoxyadenosine, deoxyguanosine, deoxythymidine, and deoxycytidine.

26. A process for cleaving DNA comprising the steps of combining an aqueous solution of the DNA cleaving reagent having the formula

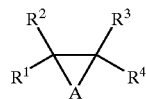

wherein A is a moiety capable of intercalation between DNA base pairs or groove binding and $R^1$, $R^2$, $R^3$ and $R^4$ are each selected from the group consisting of phenyl, substituted phenyl, $C_5$–$C_{20}$ aryl, $C_1$–$C_{20}$ alkyl, $C_1$–$C_{20}$ substituted alkyl, $C_4$–$C_8$ heterocyclic rings, and polypyrroles; at least one of said R groups being aromatic, having a concentration of from about 10 μM to about 1 M, with a solution of DNA, having a concentration of from about 1 to about 100 μM in base pairs, at a temperature of from about 20 to about 37° C., and a pH of from about 6.9 to about 8.5; and irradiating said combined solutions with light having a wavelength of from about 333 to about 550 nm from a period of from about 10 seconds to about 30 minutes.

27. A process according to claim 26 wherein, in the DNA cleaving reagent, A is a 1,4-dihydrodioxin derived from phenanthrenequinone, and at least one of said R groups is selected from substituted phenyl groups and $C_4$–$C_8$ hetero- cyclic rings.

28. A process according to claim 27 wherein said DNA cleaving reagent has the formula

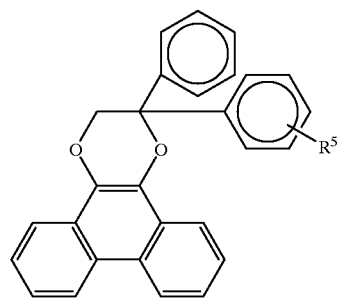

wherein $R^5$ is located in the meta or para position and is selected from the group consisting of

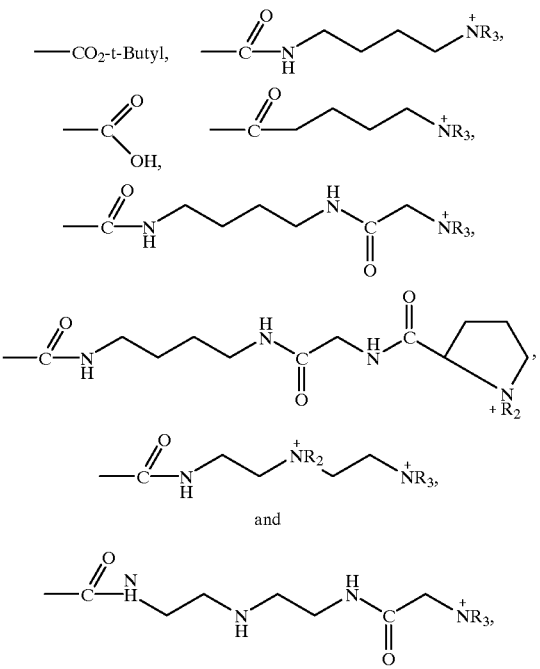

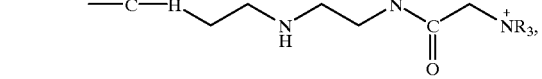

wherein R is selected from H and $C_1$–$C_4$ alkyl.

29. A process according to claim 26 wherein the DNA cleaving reagent is selected from the group consisting of

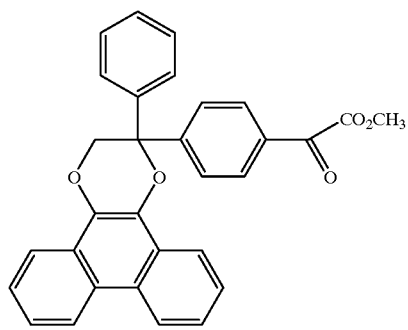

51
-continued
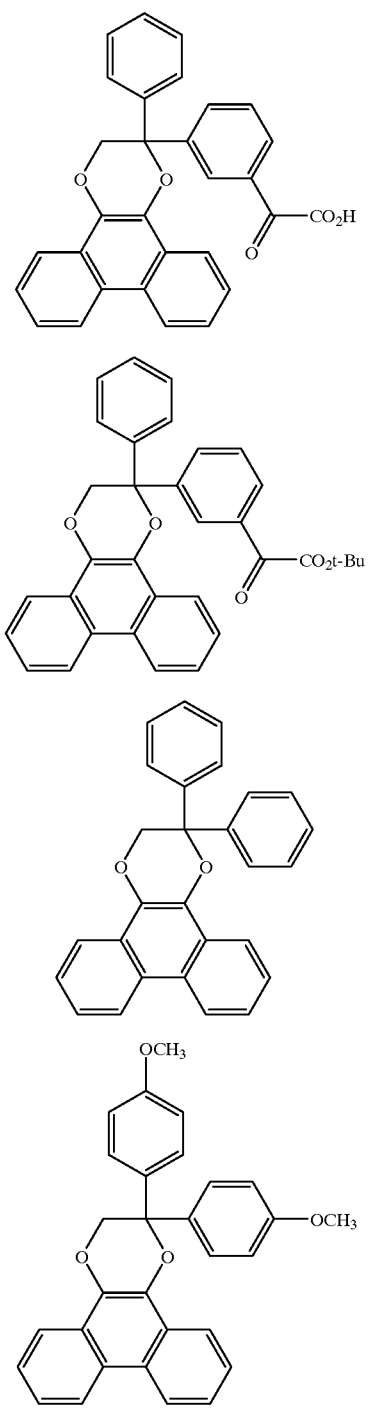
52
-continued
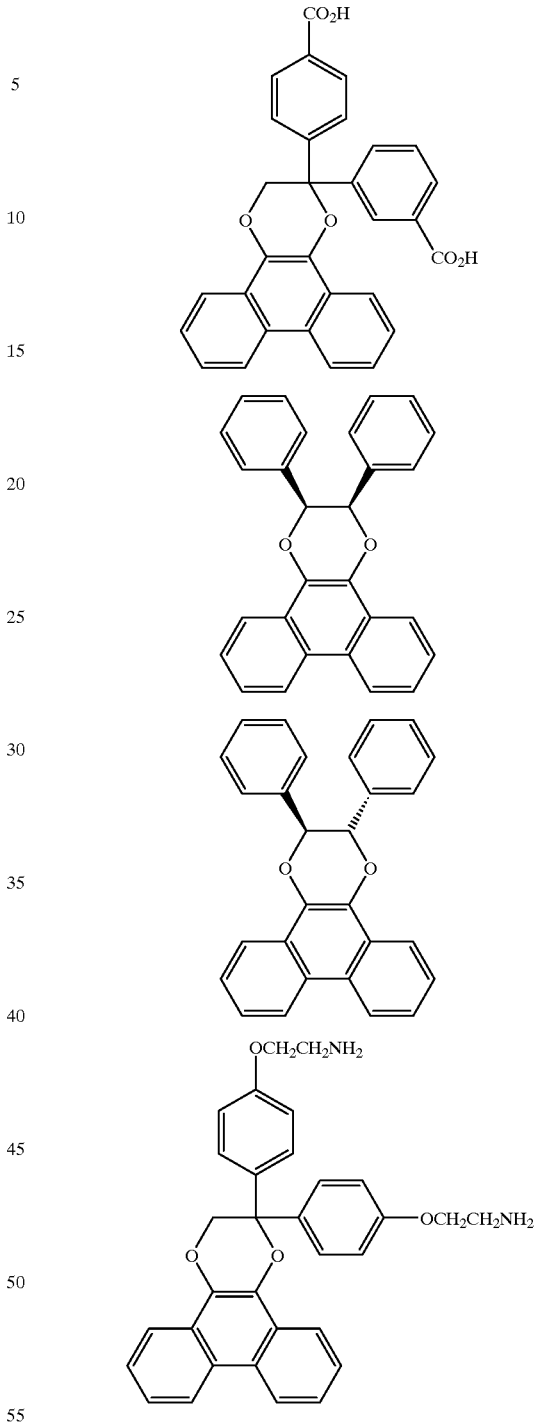

-continued

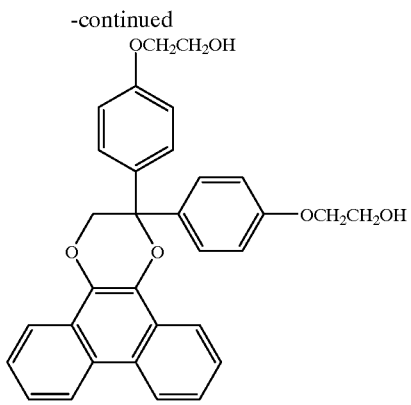

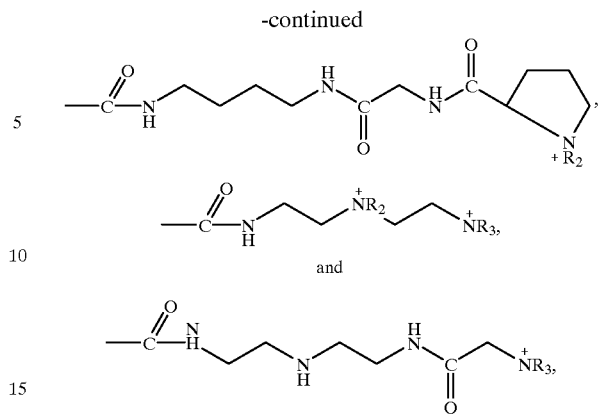

and

30. A process according to claim 26 wherein the concentration of said DNA cleaving reagent is from about 50 to about 200 $\mu$M, the concentration of DNA is from about 40 to about 50 $\mu$M in base pairs, and the temperature of the combined solutions is from about 20 to about 25° C.

31. A process according to claim 26 wherein the wavelength of the light used to irradiate the solutions is from about 333 to about 400 nm, the light has an intensity of from about 5 to about 19 mwatts/cm$^2$, and the time of irradiation is from about 5 seconds to about 2 minutes.

32. A process according to claim 26 carried out in a 100% oxygen atmosphere.

33. A DNA cleaving reagent having the formula

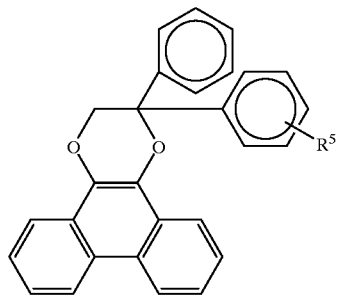

wherein R$^5$ is located in the meta or para position and is selected from the group consisting of —O—Y, —NH—Y, —CO$_2$—Y, and —C(O)NH—Y, wherein Y is a sequence-recognizing unit.

34. A DNA cleaving reagent according to claim 35 wherein R$^5$ is selected from the group consisting of

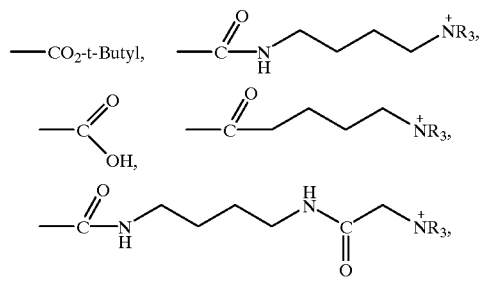

wherein R is selected from H and C$_1$–C$_4$ alkyl.

35. A DNA cleaving reagent having the formula

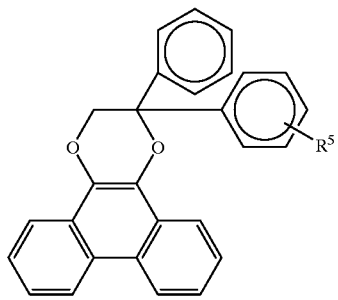

wherein R$^5$ is located in the meta or para position and is a spacer group selected from the group consisting of C$_3$ to C$_{20}$ carboxylic acid groups, ester groups, phenol groups, alkoxy groups, sulfur analogs, phosphate groups, phosphate mono- and diesters, sulfate groups, amine groups, amide groups, imide groups, urethane groups, urea groups, sulfonamide groups and phosphonamide groups, which is linked to a nucleotide selected from the group consisting of deoxyuridine, deoxyadenosine, deoxyguanosine, deoxythymidine, and deoxycytidine.

36. A DNA cleaving reagent according to claim 35 wherein R$^5$ is a C$_3$ to C$_{20}$ amine group.

37. A DNA cleaving reagent according to claim 36 wherein the R$^5$ spacer group is linked to deoxyuridine.

38. A DNA cleaving reagent according to claim 33 having the formula

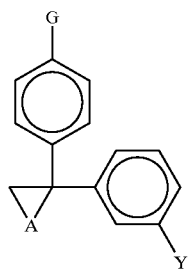

wherein Y is a DNA sequence-recognizing unit, G is a groove-jumping unit, and A is selected from the group consisting of 55
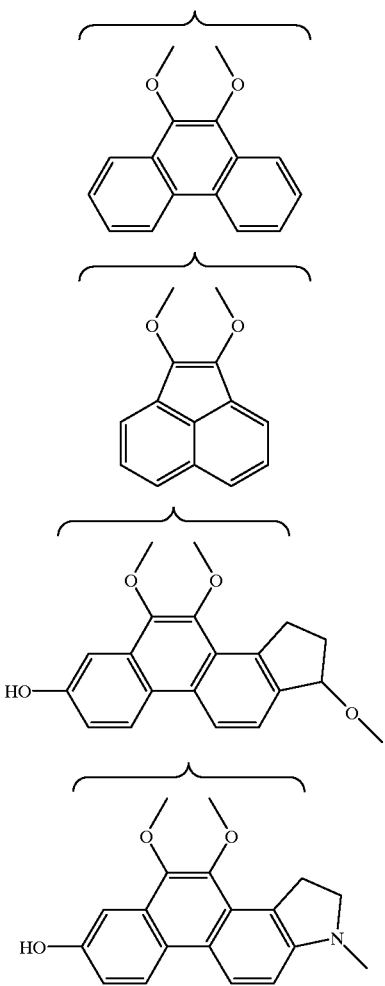
56
-continued
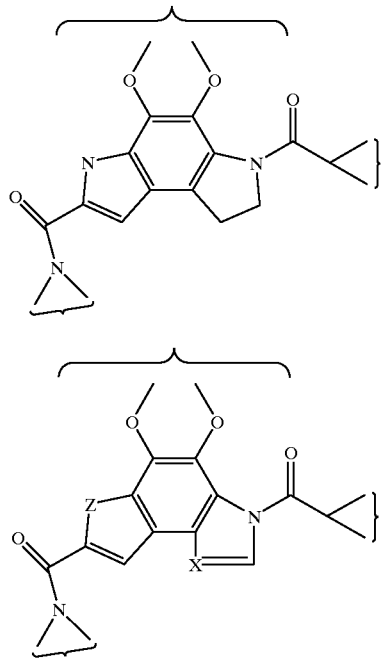
* * * * *